US008067455B2

(12) United States Patent
Xu et al.

(10) Patent No.: US 8,067,455 B2
(45) Date of Patent: *Nov. 29, 2011

(54) AMINO ACID DERIVED PRODRUGS OF PROPOFOL, COMPOSITIONS, USES AND CRYSTALLINE FORMS THEREOF

(75) Inventors: Feng Xu, Palo Alto, CA (US); Mark A. Gallop, Santa Clara, CA (US); Vivek Sasikumar, Indianapolis, IN (US); Usha Dilip, Sunnyvale, CA (US)

(73) Assignee: XenoPort, Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/572,505

(22) Filed: Oct. 2, 2009

(65) Prior Publication Data

US 2010/0087536 A1    Apr. 8, 2010

Related U.S. Application Data

(63) Continuation of application No. 11/317,418, filed on Dec. 22, 2005, now Pat. No. 7,619,110.

(60) Provisional application No. 60/639,113, filed on Dec. 23, 2004, provisional application No. 60/732,550, filed on Oct. 31, 2005.

(51) Int. Cl.
*A61K 31/415* (2006.01)

(52) U.S. Cl. ............ 514/397; 562/553; 560/46; 514/19; 514/171; 514/295; 514/299

(58) Field of Classification Search .......................... None
See application file for complete search history.

(56) References Cited

U.S. PATENT DOCUMENTS

| | | | |
|---|---|---|---|
| 3,845,770 A | 11/1974 | Theeuwes et al. | |
| 3,916,899 A | 11/1975 | Theeuwes et al. | |
| 4,765,539 A | 8/1988 | Noakes et al. | |
| 4,962,885 A | 10/1990 | Coffee | |
| 5,112,598 A | 5/1992 | Biesalski | |
| 5,556,611 A | 9/1996 | Biesalski | |
| 5,698,155 A | 12/1997 | Grosswald et al. | |
| 5,950,619 A | 9/1999 | van der Linden et al. | |
| 5,954,047 A | 9/1999 | Armer et al. | |
| 5,970,974 A | 10/1999 | van Der Linden et al. | |
| 6,254,853 B1 | 7/2001 | Hendler et al. | |
| 6,362,234 B1 | 3/2002 | Hendler | |
| 6,451,776 B2 | 9/2002 | Stella et al. | |
| 7,220,875 B2 | 5/2007 | Gallop et al. | |
| 7,230,003 B2 | 6/2007 | Xu et al. | |
| 7,241,807 B2 | 7/2007 | Xu et al. | |
| 7,550,506 B2 * | 6/2009 | Xu et al. ................. | 514/534 |
| 7,576,127 B2 | 8/2009 | Xu et al. | |
| 7,619,110 B2 | 11/2009 | Xu et al. | |
| 2008/0161400 A1 | 7/2008 | Virsik et al. | |
| 2009/0005352 A1 | 1/2009 | Xu et al. | |
| 2009/0005444 A1 | 1/2009 | Cundy et al. | |
| 2009/0076141 A1 | 3/2009 | Virsik | |
| 2009/0286763 A1 | 11/2009 | Xu et al. | |
| 2009/0312424 A1 | 12/2009 | Xu et al. | |

FOREIGN PATENT DOCUMENTS

| | | |
|---|---|---|
| WO | WO 94/12285 A2 | 6/1994 |
| WO | WO 94/14543 A2 | 7/1994 |
| WO | WO 95/26234 A1 | 10/1995 |
| WO | WO 95/26235 A1 | 10/1995 |
| WO | WO 95/32807 A1 | 12/1995 |
| WO | WO 99/58555 A2 | 11/1999 |
| WO | WO 00/48572 A1 | 8/2000 |
| WO | WO 00/54588 A1 | 9/2000 |
| WO | WO 02/13810 A1 | 2/2002 |
| WO | WO 2004/033424 A1 | 4/2004 |
| WO | WO 2007/027476 A2 | 3/2007 |
| WO | WO 2007/027477 A2 | 3/2007 |
| WO | WO 2007/052999 | 5/2007 |

OTHER PUBLICATIONS

Burton et al, Drugs Aging. 2004;21(4):229-42.*
Marik, Curr Pharm Des. 2004;10(29):3639-49.*
Alderman, A review of cellulose ethers in hydrophilic matrices for oral controlled-release dosage forms. *Int. J. Pharm. Tech. & Prod. Mfr.* (1984), 5(3), 1-9.
Altomare et al., Highly water-soluble derivatives of the anesthetic agent propofol: in vitro and in vivo evaluation of cyclic amino esters. *Eur J Pharmaceutical Sciences* (2003), 20, 17-26.
Anderson et al., α-Amino acid phenolic ester derivatives: novel water-soluble general anesthetic agents which allosterically modulate $GABA_A$ receptors. *J. Med. Chem.* (2001), 44, 3582-3591.
Balimane et al., Involvement of multiple transporters in the oral absorption of nucleoside analogues. *Adv Drug Deliv Rev* (1999), 39, 183-209.
Bamba et al., Release mechanisms in gelforming sustained release preparations. *Int. J. Pharm.* (1979), 2, 307-315.
Banaszczyk et al., Propofol phosphate, a water-soluble propofol prodrug: in vivo evaluation. *Anesth. Analg.* (2002), 95, 1285-1292.
Beilstein Handbook of Organic Chemistry, 4th Ed., Beilstein Institute of Organic Chemistry, Frankfurt, Germany, vol. 27, part 26, 1979 (5 pages).
Borgeat et al., Adjuvant propofol enables better control of nausea and emesis secondary to chemotherapy for breast cancer. *Can. J. Anaesth.* (1994), 41(11), 1117-1119.
Borgeat et al., Propofol improves patient comfort during Cisplatin chemotherapy. *Oncology* (1993), 50, 456-459.
Briggs et al., An adverse reaction to the administration of disoprofol (Diprivan). *Anaesthesia* (1982), 37, 1099-1101.
Brooker et al., Propofol maintenance to reduce postoperative emesis in thyroidectomy patients: a group sequential comparison with isoflurane/nitrous oxide. *Anaesth. Intensive Care* (1998), 26(6), 625-629.

(Continued)

*Primary Examiner* — Sudhakar Katakam
(74) *Attorney, Agent, or Firm* — Dorsey & Whitney LLP

(57) ABSTRACT

The present invention provides a prodrug of propofol and crystalline forms thereof, methods of making the propofol prodrug and crystalline forms thereof, pharmaceutical compositions of the propofol prodrug and crystalline forms thereof, methods of using the propofol prodrug and crystalline forms thereof and pharmaceutical compositions thereof to treat diseases or disorders such as headache pain, post-chemotherapy or post-operative surgery nausea and vomiting, neurodegenerative disorders, and mood disorders.

21 Claims, 2 Drawing Sheets

OTHER PUBLICATIONS

Brown et al., Role of propofol in refractory status epilepticus. *Ann. Pharmacother.* (1998), 32, 1053-1059.

De La Cruz et al., The effect of propofol on oxidative stress in platelets from surgical patients. *Anesth. Analg.* (1999), 89, 1050-1055.

During et al., Controlled release of dopamine from a polymeric brain implant: in vivo characterization. *Ann. Neurol.* (1989), 25, 351-356.

Fieser et al., Reagents for Organic Synthesis (2004), vol. 22, Wiley Interscience (10 pages).

Gan et al., Determination of plasma concentrations of propofol associated with 50% reduction in postoperative nausea. *Anesthesiology* (1997), 87, 779-784.

Gennaro Ed., Remington's Pharmaceutical Sciences, Philadelphia College of Pharmacy and Science, 19th Edition (1995), Mack Publishing Company, Easton PA (5 pages).

Greene et al., Protective Groups in Organic Synthesis, 2nd ed, John Wiley & Sons, Inc., (1991) (4 pages).

Grunberg et al., Palonosetron: a unique 5-$HT_3$-receptor antagonist for the prevention of chemotherapy-induced emesis. *Expert Opin Pharmacother* (2003), 4(12), 2297-2303.

Harrison et al., Compendium of Organic Synthetic Methods, vols. 1-8, John Wiley and Sons, Inc., 1971-1995 (32 pages).

Hasan et al., Comparison of the effects of propofol and thiopental on the pattern of maximal electroshock seizures in the rat. *Pharmacol Toxicol* (1994), 74, 50-53.

Holtkamp et al., Propofol in subanesthetic doses terminates status epilepticus in a rodent model. *Ann Neurol* (2001), 49, 260-263.

Howard et al., Intracerebral drug delivery in rats with lesion-induced memory deficits. *J. Neurosurg.* (1989), 71, 105-112.

Krusz et al., Intravenous propofol: unique effectiveness in treating intractable migraine. *Headache* (2000), 40, 224-230.

Kuisma et al., Propofol in prehospital treatment of convulsive status epilepticus. *Epilepsia* (1995), 36(12), 1241-1243.

Langer et al. (eds.), Medical Applications of Controlled Release, vols. 1 and 2, CRC Press Inc., Boca Raton, Florida (1984) (6 pages).

Langer et al., Chemical and physical structure of polymers as carriers for controlled release of bioactive agents: a review. *JMS-Rev. Macromol Chem. Phys.* (1983), C23(1), 61-126.

Langley et al., Propofol. A review of its pharmacodynamic and pharmacokinetic properties and use as an intravenous anaesthetic. *Drugs* (1988), 35, 334-372.

Larock, Comprehensive Organic Transformations. A guide to functional group preparations (1989), VCH Publishers New York, NY (20 pages).

Lee et al., Inhibitors of acyl-CoA:cholesterol O-acyl transferase (ACAT) as hypocholesterolemic agents. CI-1011: An acyl sulfamate with unique cholesterol-lowering activity in animals fed noncholesterol-supplemented diets. *J Med Chem* (1996), 39(26), 5031-5034.

Levy et al., Inhibition of calcification of bioprosthetic heart valves by local controlled-release release diphosphonate. *Science* (1985), 228, 190-192.

March, Advanced Organic Chemistry. Reactions, mechanisms and structure, 4th ed., Wiley Interscience, (1991) (5 pages).

Murphy et al., The antioxidant potential of propofol (2,6-diisopropylphenol). *Br. J. Anaesth.* (1992), 68, 613-618.

O'Neil et al. eds., The Merck Index: An encyclopedia of chemicals, drugs, and biologicals. 13th ed. (2001), pp. 156, 600, 808, 1225, and 1741-1742.

Paquette Ed., Encyclopedia of Reagents for Organic Synthesis vols. 1-8, John Wiley & Sons, New York, NY (1995) (10 pages).

Peduto et al., Biochemical and electrophysiologic evidence that propofol enhances GABAergic transmission in the rat brain. *Anesthesiology* (1991), 75, 1000-1009.

Phelps et al., Propofol in chemotherapy-associated nausea and vomiting. *Ann. Pharmacother.* (1996), 30, 290-292.

Picard et al., Prevention of pain on injection with propofol: a quantitative systematic review. *Anesth. Analg.* (2000), 90, 963-969.

Pop et al., Synthesis and preliminary pharmacological evaluation of some chemical delivery systems of 2,6-diisopropylphenol (propofol). *Med. Chem. Res.* (1992), 2, 16-21.

Raleigh et al., Pharmacokinetics of isotretinoin (iso) in rats following oral dosing or aerosol inhalation. *Proc. Amer. Assoc. Cancer Research Annual Meeting* (1999), 40, 397 (2 pages).

Raoof et al., In vivo assessment of intestinal, hepatic, and pulmonary first pass metabolism of propofol in the rat. *Pharm. Res.* (1996), 13(6), 891-895.

Sagara et al., Propofol hemisuccinate protects neuronal cells form oxidative injury. *J. Neurochem.* (1999), 73, 2524-2530.

Saudek et al., A preliminary trial of the programmable implantable medication system for insulin delivery. *N. Engl. J Med.* 1989, 321(9), 574-579.

Sefton, Implantable pumps. *CRC Crit Rev Biomed Eng.* (1987), 14(3), 201-240.

Simonian et al., Oxidative stress in neurodegenerative diseases. *Ann. Rev. Pharmacol. Toxicol.* (1996), 36, 83-106.

Smolen et al. (eds.), Controlled Drug Bioavailability: vol. 1, Drug Product Design and Performance (1984), John Wiley & Sons, New York, NY (2 pages).

Sutherland et al., Propofol and seizures. *Anaesth. Intensive Care* 1994, 22, 733-737.

Theilheimer's Synthetic Methods of Organic Chemistry, Finch Ed., vols. 1-45 (1948-1991), Karger, New York, NY (3 pages).

Theilheimer's Synthetic Methods of Organic Chemistry, Finch Ed., vol. 67 (2005), Karger, New York, NY (2 pages).

Tomioka et al., Propofol is effective in chemotherapy-induced nausea and vomiting: a case report with quantitative analysis. *Anesth. Analg.* (1999), 89, 798-799.

Tramer et al., Propofol anaesthesia and postoperative nausea and vomiting: quantitative systematic review of randomized controlled studies. *Br. J. Anaesth.* (1997), 78, 247-255.

Trapani et al., Propofol analogues. Synthesis, relationships between structure and affinity at $GABA_A$ receptor in rat brain, and differential electrophysiological profile at recombinant human $GABA_A$ receptors. *J. Med. Chem.* (1998), 41, 1846-1854.

Trapani et al., Water-soluble salts of aminoacid esters of the anaesthetic agent propofol. *Int. J. Pharm.* (1998), 175, 195-204.

Trost et al. eds., Comprehensive Organic Synthesis: Selectivity, Strategy & Efficiency in Modern Organic Chemistry, vol. 9 (1991), Pergamon Press, New York, NY (8 pages).

Verma et al., Osmotically controlled oral drug delivery. *Drug Dev. Ind. Pharm.* (2000), 26(7), 695-708.

Vippagunta et al., Crystalline solids. *Adv Drug Delivery Reviews* (2001), 48, 3-26.

Walder et al., Seizure-like phenomena and propofol: A systematic review. *Neurology* (2002), 58, 1327-1332.

Wang et al., Propofol reduces infarct size and striatal dopamine accumulation following transient middle cerebral artery occlusion: a microdialysis study. *Eur. J. Pharmacol.* (2002), 452, 303-308.

West, Solid State Chemistry and its Applications: Chapter 10, Solid Solutions (1988), John Wiley & Sons, New York, NY, pp. 358 and 365.

Young et al., Propofol neuroprotection in a rat model of ischaemia reperfusion injury. *Eur. J. Anaesthesiol.* (1997), 14, 320-326.

International Preliminary Report on Patentability (Oct. 5, 2005), Written Opinion (Jan. 25, 2005) and International Search Report of International Searching Authority (Jan. 25, 2005), in PCT Application No. PCT/US2004/002537 (7 pages).

Written Opinion and International Search Report of International Searching Authority dated Oct. 7, 2005, in PCT Application No. PCT/US2004/030999 (6 pages).

Written Opinion and International Search Report of International Searching Authority dated Jul. 11, 2005, in PCT Application No. PCT/US2005/024907 (15 pages).

International Preliminary Report on Patentability (Jan. 16, 2007), Written Opinion (Jan. 16, 2007) and International Search Report of International Searching Authority (Dec. 16, 2005), in PCT Application No. PCT/US2005/024915 (17 pages).

International Preliminary Report on Patentability (Jun. 27, 2007), Written Opinion (Jun. 27, 2007) and International Search Report of International Searching Authority (Apr. 19, 2006), in PCT Application No. PCT/US2005/047458 (12 pages).

International Preliminary Report on Patentability (Jun. 30, 2009), Written Opinion (Jun. 30, 2009) and International Search Report of International Searching Authority (Jun. 22, 2009), in PCT Application No. PCT/US2007/082365 (21 pages).
International Search Report of International Searching Authority dated Oct. 21, 2008, in PCT Application No. PCT/US2008/067380 (3 pages).
International Search Report of International Searching Authority dated Oct. 12, 2008, in PCT Application No. PCT/US2008/076236 (3 pages).
Office Action mailed Jun. 1, 2006 in U.S. Appl. No. 10/766,990 (11 pages).
Notice of Allowance mailed Sep. 26, 2006 in U.S. Appl. No. 10/766,990 (6 pages).
Office Action mailed Jul. 20, 2005 in U.S. Appl. No. 10/958,089 (11 pages).
Ex parte Quayle Action mailed Mar. 30, 2006 in U.S. Appl. No. 10/958,089 (7 pages).
Notice of Allowance mailed Feb. 1, 2007 in U.S. Appl. No. 10/958,089 (6 pages).
Office Action mailed Jan. 24, 2008 in U.S. Appl. No. 11/507,968 (14 pages).
Office Action mailed Jul. 2, 2008 in U.S. Appl. No. 11/507,968 (15 pages).
Office Action mailed Dec. 29, 2008 in U.S. Appl. No. 11/507,968 (7 pages).
Notice of Allowance mailed Apr. 7, 2009 in U.S. Appl. No. 11/507,968 (8 pages).
Notice of Allowance mailed Mar. 22, 2007 in U.S. Appl. No. 11/180,332 (18 pages).
Office Action mailed Dec. 29, 2008 in U.S. Appl. No. 11/768,713 (16 pages).
Notice of Allowance mailed Aug. 20, 2009 in U.S. Appl. No. 11/768,713 (16 pages).
Office Action mailed Aug. 29, 2007 in U.S. Appl. No. 11/180,064 (20 pages).
Office Action mailed Aug. 7, 2008 in U.S. Appl. No. 11/180,064 (6 pages).
Notice of Allowance mailed Feb. 17, 2009 in U.S. Appl. No. 11/180,064 (7 pages).
Office Action mailed Aug. 24, 2009 in U.S. Appl. No. 11/923,444 (30 pages).
Office Action mailed Jul. 31, 2008 in U.S. Appl. No. 11/317,418 (24 pages).
Office Action mailed Jan. 30, 2009 in U.S. Appl. No. 11/317,418 (13 pages).
Notice of Allowance mailed Jul. 2, 2009 in U.S. Appl. No. 11/317,418 (36 pages).

* cited by examiner

AMINO ACID DERIVED PRODRUGS OF PROPOFOL, COMPOSITIONS, USES AND CRYSTALLINE FORMS THEREOF

CROSS-REFERENCES TO RELATED APPLICATIONS

This application is a continuation application of U.S. application Ser. No. 11/317,418, now allowed, which claims the benefit under 35 U.S.C. §119(e) from U.S. Provisional Application Ser. Nos. 60/639,113 filed Dec. 23, 2004 and 60/732,550 filed Oct. 31, 2005, each of which is incorporated by reference herein in its entirety.

BACKGROUND OF THE INVENTION

The present invention provides a prodrug of propofol and crystalline forms thereof, methods of making the propofol prodrug and crystalline forms thereof, pharmaceutical compositions of the propofol prodrug and crystalline forms thereof, methods of using the propofol prodrug and crystalline forms thereof and pharmaceutical compositions thereof to treat or prevent diseases or disorders such as headache pain, post-chemotherapy or post-operative surgery nausea and vomiting neurodegenerative disorders, and mood disorders.

Propofol (2,6-diisopropylphenol), (1), is a low molecular weight phenol that is widely used as an intravenous sedative-hypnotic agent in the induction and maintenance of anesthesia and/or sedation in mammals. The advantages of propofol as an anesthetic include rapid onset of anesthesia, rapid clearance, and minimal side effects (Langley et al., *Drugs* 1988, 35, 334-372, which is incorporated by reference herein in its entirety). Propofol may mediate hypnotic effects through interaction with the GABA$_A$ receptor complex, a hetero-oligomeric ligand-gated chloride ion channel (Peduto et al., *Anesthesiology* 1991, 75, 1000-1009, which is incorporated by reference herein in its entirety).

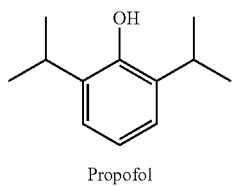

Propofol (1)

Propofol is rapidly metabolized in mammals with the drug being eliminated predominantly as glucuronidated and sulfated conjugates of propofol and 4-hydroxypropofol (Langley et al., *Drugs* 1988, 35, 334-372). Propofol clearance exceeds liver blood flow, which indicates that extrahepatic tissues contribute to the overall metabolism of the drug. Human intestinal mucosa glucuronidates propofol in vitro and oral dosing studies in rats indicate that approximately 90% of the administered drug undergoes first pass metabolism, with extraction by the intestinal mucosa accounting for the bulk of this presystemic elimination (Raoof et al., *Pharm. Res.* 1996, 13, 891-895, which is incorporated by reference herein in its entirety). Because of its extensive first-pass metabolism, propofol is administered by injection or intravenous infusion and oral administration has not been considered therapeutically effective.

Propofol has a broad range of biological and medical applications, which are evident at sub-anesthetic doses and include treatment and/or prevention of intractable migraine headache pain (Krusz et al., *Headache* 2000, 40, 224-230; Krusz, International Publication No. WO 00/54588, each of which is incorporated by reference herein in its entirety). Propofol, when used to maintain anesthesia, causes a lower incidence of post-operative nausea and vomiting (PONV) when compared to common inhalation anesthetic agents and numerous controlled clinical studies support the anti-emetic activity of propofol (Tramer et al., *Br. J. Anaesth.* 1997, 78, 247-255; Brooker et al., *Anaesth. Intensive Care* 1998, 26, 625-629; Gan et al., *Anesthesiology* 1997, 87, 779-784, each of which is incorporated by reference herein in its entirety). Propofol has also been shown to have anti-emetic activity when used in conjunction with chemotherapeutic compounds (Phelps et al., *Ann. Pharmacother.* 1996, 30, 290-292; Borgeat et al., *Oncology* 1993, 50, 456-459; Borgeat et al., *Can. J. Anaesth.* 1994, 41, 1117-1119; Tomioka et al., *Anesth. Analg.* 1999, 89, 798-799, each of which is incorporated by reference herein in its entirety). Nausea, retching and/or vomiting induced by a variety of chemotherapeutic agents (e.g., cisplatin, cyclophosphamide, 5-fluorouracil, methotrexate, anthracycline drugs, etc.) has been controlled by low-dose propofol infusion in patients refractory to prophylaxis with conventional anti-emetic drugs (e.g., serotonin antagonists and corticosteroids).

Propofol has also been used to treat patients with refractory status epilepticus (Brown et al., *Pharmacother.* 1998, 32, 1053-1059; Kuisma et al., *Epilepsia* 1995, 36, 1241-1243; Walder et al., *Neurology* 2002, 58, 1327-1332; Sutherland et al., *Anaesth. Intensive Care* 1994, 22, 733-737, each of which is incorporated by reference herein in its entirety). Further, the anticonvulsant effects of propofol have also been demonstrated in rat efficacy models at sub-anesthetic doses (Holtkamp et al., *Ann. Neurol.* 2001, 49, 260-263; Hasan et al., *Pharmacol. Toxicol.* 1994, 74, 50-53, each of which is incorporated by reference herein in its entirety).

Propofol has also been used as an antioxidant (Murphy et al., *Br. J. Anaesth.* 1992, 68, 613-618; Sagara et al., *J. Neurochem.* 1999, 73, 2524-2530; Young et al., *Eur. J. Anaesthesiol.* 1997, 14, 320-326; Wang et al., *Eur. J. Pharmacol.* 2002, 452, 303-308, each of which is incorporated by reference herein in its entirety). Propofol, at doses typically used for surgical anesthesia, has observable antioxidant effects in humans (De la Cruz et al., *Anesth. Analg.* 1999, 89, 1050-1055, which is incorporated by reference herein in its entirety). Pathogenesis or subsequent damage pathways in various neurodegenerative diseases involve reactive oxygen species and accordingly may be treated or prevented with antioxidants (Simonian et al., *Pharmacol. Toxicol.* 1996, 36, 83-106, which is incorporated by reference herein in its entirety). Examples of specific neurodegenerative diseases, which may be treated or prevented with anti-oxidants include, but are not limited to, Friedrich's disease, Parkinson's disease, Alzheimer's disease, Huntington's disease, amyotrophic lateral sclerosis (ALS), multiple sclerosis (MS), Pick's disease, inflammatory diseases, and diseases caused by inflammatory mediators such as tumor necrosis factor (TNF) and IL-1.

A significant problem with the formulation and use of propofol is poor water solubility. Accordingly, propofol must be specially formulated in aqueous media using solubilizers or emulsifiers (Briggs et al., *Anaesthesia* 1982, 37, 1099-1101). For example, in a current commercial product (Diprivan®, Astra-Zeneca) an oil-in-water emulsion (the emulsifier is the lecithin mixture Intralipid®), is used to formulate propofol (Picard et al., *Anesth. Analg.* 2000, 90, 963-969). Unfortunately, the oil-in-water emulsion formulation causes discomfort and pain at the site of injection.

One potential solution to the poor water solubility of propofol, which avoids the use of additives, solubilizers or emulsifiers and the attendant injection site pain, is a water-soluble, stable propofol prodrug that is converted to propofol in vivo. (Hendler et al., International Publication No. WO 99/58555; Morimoto et al., International Publication No. WO 00/48572; Hendler et al., U.S. Pat. No. 6,254,853; Stella et al., United States Patent Application No. US2001/0025035; Hendler, U.S. Pat. No. 6,362,234; Hendler, International Publication No. WO 02/13810; Sagara et al., *J. Neurochem.* 1999, 73, 2524-2530; Banaszczyk et al., *Anesth. Analg.* 2002, 95, 1285-1292; Trapani et al., *Int. J. Pharm.* 1998, 175, 195-204; Trapani et al., *J. Med. Chem.* 1998, 41, 1846-1854; Anderson et al., *J. Med. Chem.* 2001, 44, 3582-3591; and Pop et al., *Med. Chem. Res.* 1992, 2, 16-21). Propofol prodrugs that are sufficiently labile under physiological conditions to provide therapeutically effective concentrations of propofol, particularly when the prodrug is orally administered, have been described (Gallop et al., U.S. patent application Ser. No. 10/766,990, which is incorporated by reference herein in its entirety).

In general, crystalline forms of drugs are preferred over amorphous forms of drugs, in part, because of their superior stability. For example, in many situations, an amorphous drug converts to a crystalline drug form upon storage. Because amorphous and crystalline forms of a drug typically have differing physical/chemical properties, potencies and/or bioavailabilities, such interconversion is undesirable for safety reasons in pharmaceutical administration. A key characteristic of any crystalline drug substance is the polymorphic behavior of such a material. Polymorphs are crystals of the same molecule, which have different physical properties because the crystal lattice contains a different arrangement of molecules. The different physical properties exhibited by polymorphs affect important pharmaceutical parameters such as storage, stability, compressibility, density (important in formulation and product manufacturing) and dissolution rates (important in determining bioavailability). Stability differences may result from changes in chemical reactivity (e.g., differential hydrolysis or oxidation, such that a dosage form discolors more rapidly when comprised of one polymorph than when comprised of another polymorph), mechanical changes (e.g., tablets crumble on storage as a kinetically favored crystalline form converts to thermodynamically more stable crystalline form) or both (e.g., tablets of one polymorph are more susceptible to breakdown at high humidity). Solubility differences between polymorphs may, in extreme situations, result in transitions to crystalline forms that lack potency or are toxic. In addition, the physical properties of the crystalline form may be important in pharmaceutical processing. For example, a particular crystalline form may form solvates more readily or may be more difficult to filter and wash free of impurities than other forms (i.e., particle shape and size distribution might be different between one crystalline form relative to other forms).

room Agencies such as the United States Food and Drug Administration can require that the polymorphic content of a drug product be monitored and controlled if the most thermodynamically stable polymorphic form of the drug is not used and/or different polymorphic forms of the drug can affect the quality, safety, and/or efficacy of the drug product. Thus medical and commercial reasons favor synthesizing and marketing solid drugs as the thermodynamically stable polymorph, substantially free of kinetically favored polymorphs.

Accordingly, a need exists for a new propofol prodrug and crystalline forms thereof. The crystalline forms thereof can exhibit have superior physicochemical properties that may be used advantageously in pharmaceutical processing and pharmaceutical compositions. These prodrug and crystalline forms thereof should be sufficiently labile under physiological conditions to provide therapeutically effective concentrations of propofol, particularly when the prodrug is orally administered.

The propofol prodrug 2-amino-3-(2,6-diisopropylphenoxycarbonyloxy)-propanoic acid or pharmaceutically acceptable salts, or solvates thereof and crystalline forms thereof are provided that satisfies these and other needs. Further provided are pharmaceutical compositions of 2-amino-3-(2,6-diisopropylphenoxycarbonyloxy)-propanoic acid or pharmaceutically acceptable salts, or solvates thereof and crystalline forms thereof, methods of using crystalline forms of 2-amino-3-(2,6-diisopropylphenoxycarbonyloxy)-propanoic acid or pharmaceutically acceptable salts, or solvates thereof (including pharmaceutical compositions thereof) to treat or prevent various diseases, and methods of making crystalline forms of 2-amino-3-(2,6-diisopropylphenoxycarbonyloxy)-propanoic acid or pharmaceutically acceptable salts, or solvates thereof.

In one aspect, the propofol prodrug 2-amino-3-(2,6-diisopropylphenoxycarbonyloxy)-propanoic acid or a pharmaceutically acceptable salt thereof, or a solvate of any of the foregoing is provided.

In another aspect, crystalline forms of 2-amino-3-(2,6-diisopropylphenoxycarbonyloxy)-propanoic acid hydrochloride are provided. In some embodiments, a crystalline form of the hydrochloride salt of (S)-2-amino-3-(2,6-diisopropylphenoxycarbonyloxy)-propanoic acid having characteristic peaks (2θ) at 5.1°±0.2°, 9.7°±0.2°, 11.0°±0.2°, 14.1°±0.2°, 15.1°±0.2°, 15.8°±0.2°, 17.9°±0.2°, 18.5°±0.2°, 19.4°±0.2°, 20.1°±0.2°, 21.3°±0.2°, 21.7°±0.2°, 22.5°±0.2°, 23.5°±0.2°, 24.4°±0.2°, 25.1°±0.2°, 26.8°±0.2°, 27.3°±0.2°, 27.8°±0.2°, 29.2°±0.2°, 29.6°±0.2°, 30.4°±0.2°, and 33.4°±0.2° in an X-ray powder diffraction pattern, as substantially shown in FIG. 1 is provided.

In another aspect, crystalline forms of 2-amino-3-(2,6-diisopropylphenoxycarbonyloxy)-propanoic acid mesylate are provided. In some embodiments, a crystalline form of the mesylate salt of (S)-2-amino-3-(2,6-diisopropylphenoxycarbonyloxy)-propanoic acid having characteristic peaks (2θ) at 4.2°±0.1°, 11.7°±0.1°, 12.1°±0.1°, 12.6°±0.1°, 16.8°±0.1°, 18.4°±0.2°, 21.0°±0.1°, 22.3°±0.1°, 22.8°±0.2°, 24.9°±0.2°, 25.3°±0.1°, 26.7°±0.2°, and 29.6°±0.1° in an X-ray powder diffraction pattern, as substantially shown in FIG. 2 is provided.

In still another aspect, pharmaceutical compositions of the propofol prodrug 2-amino-3-(2,6-diisopropylphenoxy-carbonyloxy)-propanoic acid or a pharmaceutically acceptable salt thereof, or a solvate of any of the foregoing is provided or a crystalline form of any of the foregoing are provided. The pharmaceutical compositions comprise a therapeutically effective amount of 2-amino-3-(2,6-diisopropylphenoxycarbonyloxy)-propanoic acid or a pharmaceutically acceptable salt thereof, or a solvate of any of the foregoing or a crystalline form of any of the foregoing and a pharmaceutically acceptable vehicle. In certain embodiments, a pharmaceutical composition comprising crystalline (S)-2-amino-3-(2,6-diisopropylphenoxy-carbonyloxy)-propanoic acid hydrochloride having characteristic absorption peaks, supra, and a pharmaceutically acceptable vehicle is provided. In certain embodiments, a pharmaceutical composition comprising crystalline (S)-2-amino-3-(2,6-diisopropylphenoxycarbonyloxy)-propanoic acid mesylate having characteristic absorption peaks, supra, and a pharmaceutically acceptable vehicle is provided.

In still another aspect, methods for treating or preventing various diseases or disorders are provided. The methods are useful for treating or preventing diseases or disorders including, but not limited to, headache pain such as migraine, post-chemotherapy or post-operative surgery nausea and vomiting, mood disorders such as depression, and neurodegenerative disorders (e.g., epilepsy, Friedrich's disease, Parkinson's disease, Alzheimer's disease, Huntington's disease, amyotrophic lateral sclerosis (ALS), multiple sclerosis (MS), Pick's disease, etc.). In certain embodiments methods involve administering to a patient in need of such treatment or prevention a therapeutically effective amount of 2-amino-3-(2,6-diisopropylphenoxycarbonyloxy)-propanoic acid hydrochloride or crystalline forms thereof, or pharmaceutical compositions thereof. In some embodiments, crystalline (S)-2-amino-3-(2,6-diisopropylphenoxycarbonyloxy)-propanoic acid hydrochloride or pharmaceutical compositions thereof with the characteristic absorption peaks, supra, is administered to the patient in need of such treatment. In certain embodiments the methods involve administering to a patient in need of such treatment or prevention a therapeutically effective amount of 2-amino-3-(2,6-diisopropylphenoxycarbonyloxy)-propanoic acid mesylate or crystalline forms thereof, or pharmaceutical compositions thereof. In some embodiments, crystalline (S)-2-amino-3-(2,6-diisopropylphenoxycarbonyloxy)-propanoic acid mesylate or pharmaceutical compositions thereof with the characteristic absorption peaks, supra, is administered to the patient in need of such treatment.

In still another aspect, methods for inducing and/or maintaining anesthesia or sedation in a mammal are provided. In certain embodiments, the methods involve administering to a patient in need of such anesthesia or sedation induction and/or maintenance a therapeutically effective amount of 2-amino-3-(2,6-diisopropylphenoxy-carbonyloxy)-propanoic acid hydrochloride or crystalline forms thereof, or pharmaceutical compositions thereof. In certain embodiments, crystalline (S)-2-amino-3-(2,6-diisopropylphenoxycarbonyloxy)-propanoic acid hydrochloride with characteristic absorption peaks, supra, is administered to the patient in need of such treatment. In certain embodiments, the methods involve administering to a patient in need of such anesthesia or sedation induction and/or maintenance a therapeutically effective amount of 2-amino-3-(2,6-diisopropylphenoxycarbonyloxy)-propanoic acid mesylate or crystalline forms thereof, or pharmaceutical compositions thereof. In some embodiments, crystalline (S)-2-amino-3-(2,6-diisopropylphenoxycarbonyloxy)-propanoic acid mesylate with characteristic absorption peaks, supra, is administered to the patient in need of such treatment.

In still another aspect, methods for making 2-amino-3-(2,6-diisopropylphenoxycarbonyloxy)-propanoic acid and/or crystalline forms thereof are provided.

These and other features of the present disclosure are set forth herein.

DETAILED DESCRIPTION

Definitions

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the properties sought to be obtained. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the embodiments are approximations, the numerical values set forth in the specific examples are reported as precisely as possible. Any numerical values, however, inherently contain certain errors necessarily resulting from the standard deviation found in their respective testing measurements.

The section headings used herein are for organizational purposes only, and are not to be construed as limiting the subject matter disclosed.

To the extent the definitions of terms in the publications, patents, and patent applications incorporated herein by reference are not the same as the definitions set forth in this specification, the definitions in this specification control for the entire specification, including the claims. Any other definitions in the publications, patents, and patent applications incorporated herein by reference that are not explicitly provided in this specification apply only to the embodiments discussed in the publications, patents, and patent applications incorporated herein by reference.

"2-Amino-3-(2,6-diisopropylphenoxycarbonyloxy)-propanoic acid" refers to pharmaceutically acceptable salts of 2-amino-3-(2,6-diisopropylphenoxycarbonyloxy)-propanoic acid, to pharmaceutically acceptable solvates of any of the foregoing, and to crystalline forms of any of the foregoing.

"2-Amino-3-(2,6-diisopropylphenoxycarbonyloxy)-propanoic acid salt" refers to pharmaceutically acceptable salts of 2-amino-3-(2,6-diisopropylphenoxycarbonyloxy)-propanoic acid and crystalline forms thereof. In certain embodiments 2-amino-3-(2,6-diisopropylphenoxycarbonyloxy)-propanoic acid salt refers to the hydrochloride salt, the mesylate salt, or the trifluoroacetate salt of 2-amino-3-(2,6-diisopropylphenoxycarbonyloxy)-propanoic acid.

"Enantiomeric purity" refers to the percent of one enantiomer of a compound relative to all other enantiomers of the compound in a composition containing more than one enantiomer of the compound. For example, a composition has an enantiomeric purity of 97% of (S)-2-amino-3-(2,6-diisopropylphenoxycarbonyloxy)-propanoic acid hydrochloride when 97% of the 2-amino-3-(2,6-diisopropylphenoxycarbonyloxy)-propanoic acid hydrochloride in the composition is the (S)-2-amino-3-(2,6-diisopropylphenoxycarbonyloxy)-propanoic acid enantiomer and 3% of the 2-amino-3-(2,6-diisopropylphenoxycarbonyloxy)-propanoic acid hydrochloride in the composition comprises one or more of the other isomers such as the (R)-isomer. In certain embodiments, the enantiomeric purity is, for example, greater than or at least 90%, at least about 91%, at least about 92%, at least about 93%, at least about 94%, at least about 95%, at least about 96%, at least about 97%, at least about 98%, or at least about 99%.

"Pharmaceutical composition" refers to 2-amino-3-(2,6-diisopropylphenoxycarbonyloxy)-propanoic acid or a pharmaceutically acceptable salt thereof, or a solvate of any of the foregoing or crystalline forms thereof and a pharmaceutically acceptable vehicle, with which the compound is administered to a patient.

"Pharmaceutically acceptable salt" refers to a salt of 2-amino-3-(2,6-diisopropylphenoxycarbonyloxy)-propanoic acid that possesses the desired pharmacological activity of the parent compound. Such salts include but are not limited to: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, trifluoroacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound is replaced by a metal ion, e.g., an alkali metal ion, an alkaline earth ion, or an aluminum ion; or coordinates with an organic base such as ethanolamine, diethanolamine, triethanolamine, N-methylglucamine, and the like. In certain embodiments, a pharmaceutically acceptable salt can be the salt formed with hydrochloric acid, methanesulfonic acid, or trifluoroacetic acid.

"Pharmaceutically acceptable vehicle" refers to a diluent, adjuvant, excipient, or carrier with which 2-amino-3-(2,6-diisopropylphenoxycarbonyloxy)-propanoic acid or a pharmaceutically acceptable salt thereof, or a solvate of any of the foregoing or crystalline forms thereof are administered to patient.

"Patient" includes animals and mammals, for example humans.

"Preventing" or "prevention" refers to a reduction in risk of acquiring a disease or disorder (i.e., causing at least one of the clinical symptoms of the disease not to develop in a patient that may be exposed to or predisposed to the disease but does not yet experience or display symptoms of the disease).

"Prodrug" refers to a derivative of a drug molecule that requires a transformation within the body to release the active drug. Prodrugs are frequently, although not necessarily, pharmacologically inactive until converted to the parent drug. A hydroxyl-containing drug may be converted to, for example, to an ester, carbonate, acyloxyalkyl or a sulfonate prodrug, which may be hydrolyzed in vivo to provide the hydroxyl compound. Prodrugs for drugs with functional groups different than those listed above are well known to the skilled artisan.

"Promoiety" refers to a form of protecting group that when used to mask a functional group within a drug molecule converts the drug into a prodrug. Typically, the promoiety will be attached to the drug via bond(s) that are cleaved by enzymatic or non-enzymatic means in vivo.

"Protecting group" refers to a grouping of atoms that when attached to a reactive functional group in a molecule masks, reduces or prevents reactivity of the functional group. Examples of protecting groups can be found in Green et al., "Protective Groups in Organic Chemistry", (Wiley, 2$^{nd}$ ed. 1991) and Harrison et al., "Compendium of Synthetic Organic Methods", Vols. 1-8 (John Wiley and Sons, 1971-1996). Representative amino protecting groups include, but are not limited to, formyl, acetyl, trifluoroacetyl, benzyl, benzyloxycarbonyl (CBz), tert-butoxycarbonyl (Boc), trimethylsilyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC), and the like. Representative hydroxy protecting groups include, but are not limited to, those where the hydroxy group is either acylated or alkylated such as benzyl, and trityl ethers as well as alkyl ethers, tetrahydropyranyl ethers, trialkylsilyl ethers, and allyl ethers.

"Solvate" refers to a molecular complex of a compound with one or more solvent molecules in a stoichiometric or non-stoichiometric amount. Such solvent molecules are those commonly used in the pharmaceutical art, which are known to be innocuous to a recipient, e.g., water, ethanol, and the like. A molecular complex of a compound or moiety of a compound and a solvent can be stabilized by non-covalent intra-molecular forces such as, for example, electrostatic forces, van der Waals forces, or hydrogen bonds. The term "hydrate" refers to a complex where the one or more solvent molecules are water.

"Therapeutically effective amount" means the amount of a compound that, when administered to a patient for treating or preventing a disease in the patient, is sufficient to effect such treatment or prevention of the disease. The "therapeutically effective amount" will vary depending on the compound, the disease and its severity and the age, weight, etc., of the patient having the disease to be treated or prevented.

"Treating" or "treatment" of any disease or disorder refers to one or more of the following: (1) ameliorating the disease or disorder (i.e., arresting or reducing the development of the disease or at least one of the clinical symptoms thereof); (2) ameliorating at least one physical parameter, which may not be discernible by the patient; (3) inhibiting the disease or disorder, either physically, (e.g., stabilization of a discernible symptom), physiologically, (e.g., stabilization of a physical parameter), or both; and (4) delaying the onset of the disease or disorder.

Reference will now be made in detail to certain embodiments of compounds, compositions, and methods. The disclosed embodiments are not intended to be limiting of the claims. To the contrary, the claims are intended to cover all alternatives, modifications, and equivalents of the disclosed embodiments.

COMPOUNDS

Figure 1:
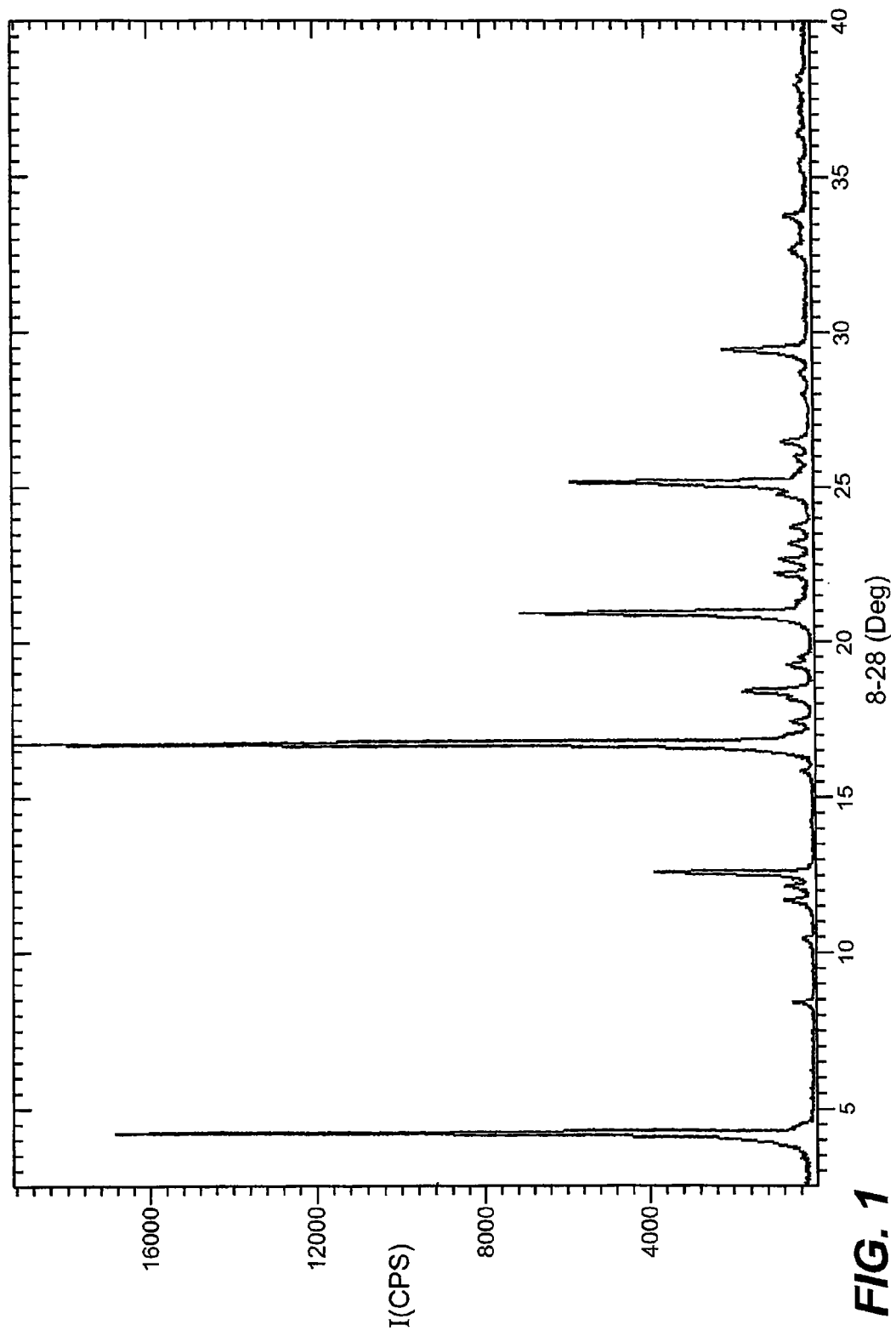
FIG. 1 illustrates an X-ray powder diffraction pattern of crystalline (S)-2-amino-3-(2,6-diisopropylphenoxycarbonyloxy)-propanoic acid hydrochloride.

The propofol prodrug 2-amino-3-(2,6-diisopropylphenoxycarbonyloxy)-propanoic acid (2) or pharmaceutically acceptable salts thereof, or pharmaceutically acceptable solvates of any of the foregoing, are disclosed herein.

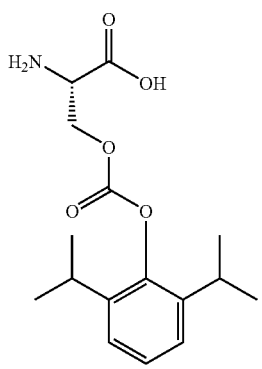

(2)

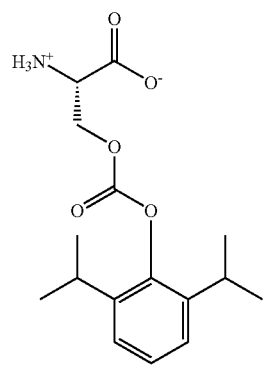

(3)

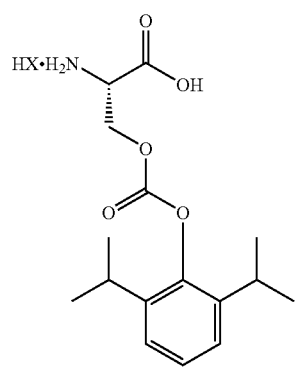

(4)

The skilled artisan will appreciate that although (S)-2-amino-3-(2,6-diisopropylphenoxycarbonyloxy)-propanoic acid is depicted, supra, all possible enantiomers and stereoisomers of 2-amino-3-(2,6-diisopropylphenoxy-carbonyloxy)-propanoic acid including the stereoisomerically pure form (e.g., enantiomerically pure) and enantiomeric mixtures, including the racemic form, are encompassed by the description herein unless specifically excluded. 2-Amino-3-(2,6-diisopropylphenoxy-carbonyloxy)-propanoic acid may exist in several tautomeric forms. Accordingly, all possible tautomeric forms of 2-amino-3-(2,6-diisopropylphenoxycarbonyloxy)-propanoic acid are encompassed herein unless otherwise specified. All isotopically labeled forms of 2-amino-3-(2,6-diisopropylphenoxycarbonyloxy)-propanoic acid are also encompassed herein unless otherwise specified. Examples of isotopes that may be incorporated into 2-amino-3-(2,6-diisopropylphenoxycarbonyloxy)-propanoic acid include, but are not limited to, $^2H$, $^3H$, $^{11}C$, $^{13}C$, $^{14}C$, $^{15}N$, $^{18}N$, $^{18}O$, and $^{17}O$.

Those of ordinary skill in the art will appreciate that 2-amino-3-(2,6-diisopropylphenoxycarbonyloxy)-propanoic acid (2) may exist as a zwitterionic species (i.e., as compound (3)) or may be readily converted to a protic acid addition salt (i.e., as compound (4), where X is an anionic moiety). Protic acids suitable for forming salts of compound (4) include inorganic acids such as, for example, hydrochloric acid, hydrobromic acid, sulfuric acid, nitric acid, phosphoric acid, and the like; or organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like. Generally, protic acids suitable for forming salts of compound (4) typically have pKa values less than 4.0 and include, but are not limited to the aforementioned inorganic acids and sulfonic acids.

The acid addition salts (4) may be advantageously utilized as propofol prodrugs since they are stabilized with regard to spontaneous cyclization relative to compounds (2) and (3) (see Scheme 1).

Scheme 1

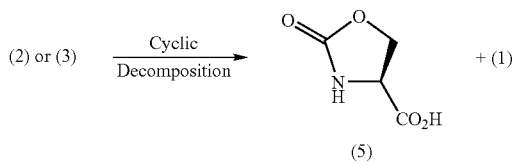

In certain embodiments, the hydrochloride salt of 2-amino-3-(2,6-diisopropyl-phenoxycarbonyloxy)-propanoic acid is provided. In certain embodiments, the hydrochloride salt of (S)-2-amino-3-(2,6-diisopropylphenoxycarbonyloxy)-propanoic acid (i.e., compound (6)) is provided. In certain embodiments, the mesylate salt of 2-amino-3-(2,6-diisopropylphenoxycarbonyloxy)-propanoic acid is provided. In certain embodiments, the mesylate salt of (S)-2-amino-3-(2,6-diisopropylphenoxy-carbonyloxy)-propanoic acid (i.e., compound (7)) is provided. In certain embodiments, the trifluoroacetate salt of 2-amino-3-(2,6-diisopropylphenoxy-carbonyloxy)-propanoic acid is provided. In certain embodiments, the trifluoroacetate salt of (S)-2-amino-3-(2,6-diisopropylphenoxycarbonyloxy)-propanoic acid (i.e., compound (8)) is provided.

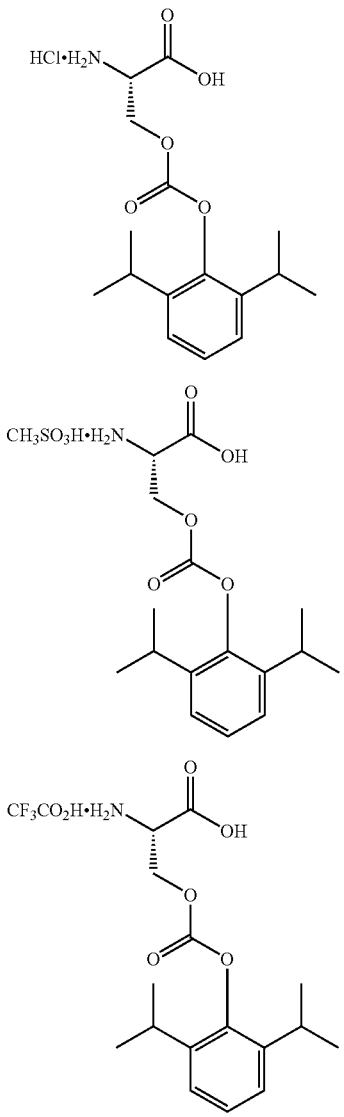

In certain embodiments, crystalline forms of 2-amino-3-(2,6-diisopropyl-phenoxycarbonyloxy)-propanoic acid or pharmaceutically acceptable salts, or solvates thereof are provided. In certain embodiments, crystalline forms of (S)-2-amino-3-(2,6-diisopropylphenoxycarbonyloxy)-propanoic acid or pharmaceutically acceptable salts, or solvates thereof are provided.

In certain embodiments, crystalline 2-amino-3-(2,6-diisopropylphenoxycarbonyloxy)-propanoic acid hydrochloride is provided. In certain embodiments, crystalline (S)-2-amino-3-(2,6-diisopropylphenoxycarbonyloxy)-propanoic acid hydrochloride (6) is provided. In certain embodiments, crystalline (S)-2-amino-3-(2,6-diisopropylphenoxy-carbonyloxy)-propanoic acid hydrochloride is provided having characteristic peaks (2θ) at 5.1°±0.2°, 9.7°±0.2°, 11.0°±0.2°, 14.1°±0.2°, 15.1°±0.2°, 15.8°±0.2°, 17.9°±0.2°, 18.5°±0.2°, 19.4°±02°, 20.1°±0.2°, 21.3°±0.2°, 21.7°±0.2°, 22.5°±0.2°, 23.5°±0.2°, 24.2°±0.2°, 25.1°±0.2°, 26.8°±0.2°, 27.3°±0.2°, 27.8°±0.2°, 29.2°±0.2°, 29.6°±0.2°, 30.4°±0.2°, and 33.4°±0.2° in an X-ray powder diffraction pattern, as substantially shown in FIG. 1. In certain embodiments, crystalline (S)-2-amino-3-(2,6-diisopropylphenoxycarbonyloxy)-propanoic acid hydrochloride is provided having characteristic peaks (2θ) at 5.1°±0.2°, 9.7°±0.2°, 11.0°±0.2°, 14.1°±0.2°, 15.1°±0.2°, 15.8°±0.2°, 17.9°±0.2°, 18.5°±0.2°, 20.1°±0.2°, 22.5°±0.2°, 23.5°±0.2°, 25.1°±0.2°, 29.2°±0.2°, 29.6°±0.2°, and 33.4°±0.2° in an X-ray powder diffraction pattern.

In certain embodiments, crystalline 2-amino-3-(2,6-diisopropylphenoxycarbonyloxy)-propanoic acid hydrochloride is provided having a melting point from about 180° C. to about 200° C. In certain embodiments, crystalline 2-amino-3-(2,6-diisopropylphenoxycarbonyloxy)-propanoic acid hydrochloride is provided having a melting point from about 185° C. to about 195° C. In certain embodiments, crystalline (S)-2-amino-3-(2,6-diisopropylphenoxycarbonyloxy)-propanoic acid hydrochloride is provided having a melting point from about 188° C. to about 189° C.

In certain embodiments, crystalline 2-amino-3-(2,6-diisopropylphenoxycarbonyloxy)-propanoic acid mesylate is provided. In certain embodiments, crystalline (S)-2-amino-3-(2,6-diisopropylphenoxycarbonyloxy)-propanoic acid mesylate (7) is provided. In certain embodiments, crystalline (S)-2-amino-3-(2,6-diisopropylphenoxycarbonyloxy)-propanoic acid mesylate is provided having characteristic peaks (2θ) at 4.2°±0.1°, 11.7°±0.1°, 12.1°±0.1°, 12.6°±0.1°, 16.8°±0.1°, 18.4°±0.2°, 21.0°±0.1°, 22.3°±0.1°, 22.8°±0.2°, 24.9°±0.2°, 25.3°±0.1°, 26.7°±0.2°, and 29.6°±0.1° in an X-ray powder diffraction pattern, as substantially shown in FIG. 2. In certain embodiments, crystalline (S)-2-amino-3-(2,6-diisopropylphenoxycarbonyloxy)-propanoic acid mesylate is provided having characteristic peaks (2θ) at 4.2°±0.1°, 12.6°±0.1°, 16.8°±0.1°, 21.0°±0.1°, 25.3°±0.1°, 2 and 29.6°±0.1° in an X-ray powder diffraction pattern.

In certain embodiments, crystalline 2-amino-3-(2,6-diisopropylphenoxycarbonyloxy)-propanoic acid mesylate is provided having a melting point from about 156° C. to about 176° C. In certain embodiments, crystalline 2-amino-3-(2,6-diisopropylphenoxycarbonyloxy)-propanoic acid mesylate is provided having a melting point from about 161° C. to about 172° C. In certain embodiments, crystalline (S)-2-amino-3-(2,6-diisopropylphenoxycarbonyloxy)-propanoic acid mesylate is provided having a melting point from about 166° C. to about 167° C.

In certain embodiments, the crystalline 2-amino-3-(2,6-diisopropylphenoxycarbonyloxy)-propanoic acid salt is more stable at room temperature and humidity than the corresponding non-crystalline 2-amino-3-(2,6-diisopropylphenoxycarbonyloxy)-propanoic acid salt. In certain embodiments, the crystalline hydrochloride, mesylate, or trifluoroacetic acid salt of 2-amino-3-(2,6-diisopropylphenoxycarbonyloxy)-propanoic acid, is more stable at room temperature and humidity than the corresponding non-crystalline hydrochloride, mesylate, or trifluoroacetic acid salt of 2-amino-3-(2,6-diisopropylphenoxycarbonyloxy)-propanoic acid.

In certain embodiments, crystalline 2-amino-3-(2,6-diisopropylphenoxy-carbonyloxy)-propanoic acid salt may be prepared by first adding 2-amino-3-(2,6-diisopropylphenoxycarbonyloxy)-propanoic acid salt to a solvent to form a solution or suspension. As used herein, the terms solution and suspension are used interchangeably and are meant to include embodiments where 2-amino-3-(2,6-diisopropylphenoxycarbonyloxy)-propanoic acid salt is placed in a solvent or solvent mixture regardless of solubility.

The solvent used in crystallization may be either a homogenous solvent, a combination of solvents, or a solvent or solvent combination in which the 2-amino-3-(2,6-diisopropylphenoxycarbonyloxy)-propanoic acid salt exhibits temperature dependent solubility. In certain embodiments, the solvent can be selected from water, methanol, ethanol, 1,2-propane diol, t-butanol, n-butanol, isopropanol, acetic acid, dimethylsulfoxide, dimethylformamide, N-methylpyrrolidone, 2-ethoxyethanol, 1,2-ethanediol, 2-methoxyethanol, or mixtures of any of the foregoing. In certain embodiments, the solvent comprises a solvent mixture.

In certain embodiments, solvents or solvent combinations in which 2-amino-3-(2,6-diisopropylphenoxycarbonyloxy)-propanoic acid salt is soluble within a first temperature range and poorly soluble within a second temperature range, can be advantageously used in the methods disclosed herein. Mixtures of a "good" solvent and an "anti-solvent" can also be used with temperature dependent solubilization, i.e., dissolving at elevated temperature and crystallizing at room temperature. Examples of suitable "good" solvents include water, methanol, ethanol, 1,2-propane diol, t-butanol, n-butanol, isopropanol, acetic acid, dimethylsulfoxide, dimethylformamide, N-methylpyrrolidone, 2-ethoxyethanol, 1,2-ethanediol, 2-methoxyethanol, and mixtures of any of the foregoing. Examples of suitable "anti-solvents" include alkanes such as pentane, hexane, heptane, octane, nonane, decane, undecane, dodecane, cis- or trans-decalin, cyclohexane, and methylcyclohexane; arenes such as benzene, toluene, chlorobenzene, cumene, o-xylene, m-xylene, and p-xylene; ethers such as diethylether, 1,2-dimethoxyethane, tetrahydrofuran, 2-methyl tetrahydrofuran, methyl tert-butyl ether, and 1,4-dioxane; alkyl esters such as methyl acetate, ethyl acetate, isopropyl acetate, and isobutyl acetate; and mixtures of any of the foregoing.

In certain embodiments, the dissolution process can be carried out at elevated temperature, up to and including the boiling point of the solvent or solvent combination. Accordingly, in certain embodiments, 2-amino-3-(2,6-diisopropylphenoxycarbonyloxy)-propanoic acid salt can be dissolved in a solvent or solvent mixture with heating and optionally, with shaking and stirring. The heated solution may be kept at elevated temperature to ensure complete dissolution of 2-amino-3-(2,6-diisopropylphenoxycarbonyloxy)-propanoic acid salt. The heated solution may also be filtered at elevated temperature to remove any undissolved components.

In certain embodiments, the solution is cooled slowly to provide crystalline 2-amino-3-(2,6-diisopropylphenoxycarbonyloxy)-propanoic acid salt, which may be separated from residual solvent by filtration and/or drying under reduced pressure. In certain embodiments, the solution can be cooled to about 25° C. In certain embodiments, the solution is cooled to between about 0° C. and about 25° C. Other methods, known to those of skill in the crystallization arts, (e.g., solvent evaporation, drowning, chemical reaction, seeding with a small quantity of the desired crystal form, etc.) may also be employed to provide crystalline 2-amino-3-(2,6-diisopropylphenoxycarbonyloxy)-propanoic acid salt. Although the disclosure, supra, exemplifies the crystallization of 2-amino-3-(2,6-diisopropylphenoxycarbonyloxy)-propanoic acid salt the skilled artisan will appreciate that the general procedures disclosed may be used to crystallize 2-amino-3-(2,6-diisopropylphenoxycarbonyloxy)-propanoic acid or any of its solvates, or pharmaceutically acceptable salts.

In certain embodiments, (S)-2-amino-3-(2,6-diisopropylphenoxycarbonyloxy)-propanoic acid hydrochloride (6) can be dissolved in a mixture of ethanol/toluene (about 1/10 by volume) at a temperature from about 50° C. to about the reflux temperature, and in certain embodiments at a temperature of about 80° C. In certain embodiments, the concentration of 2-amino-3-(2,6-diisopropylphenoxycarbonyloxy)-propanoic acid hydrochloride in the ethanol/toluene mixture can be from about 0.01 g/mL and about 0.10 g/mL. In certain embodiments, the concentration of (S)-2-amino-3-(2,6-diisopropylphenoxycarbonyloxy)-propanoic acid hydrochloride in the ethanol/toluene mixture can be about 0.03 g/mL. The solution can then be cooled to about 25° C. to provide crystalline (S)-2-amino-3-(2,6-diisopropylphenoxycarbonyloxy)-propanoic acid hydrochloride.

In certain embodiments, (S)-2-amino-3-(2,6-diisopropylphenoxycarbonyloxy)-propanoic acid mesylate (7) can be dissolved in a mixture of ethanol/toluene (about 3/25 by volume) at a temperature from about 80° C. to about the reflux temperature, and in certain embodiments to a temperature of about 100° C. In certain embodiments, the concentration of (S)-2-amino-3-(2,6-diisopropylphenoxycarbonyloxy)-propanoic acid mesylate in the ethanol/toluene mixture can be from about 0.05 g/mL to about 0.50 g/mL. In certain embodiments, the concentration of (S)-2-amino-3-(2,6-diisopropylphenoxy-carbonyloxy)-propanoic acid mesylate in the ethanol/toluene mixture is about 0.1 g/mL. The solution can then be cooled to about 25° C. to provide crystalline (S)-2-amino-3-(2,6-diisopropylphenoxycarbonyloxy)-propanoic acid mesylate.

In certain embodiments, supra, for making crystalline forms of 2-amino-3-(2,6-diisopropylphenoxycarbonyloxy)-propanoic acid salt, the (S)-enantiomer of 2-amino-3-(2,6-diisopropylphenoxycarbonyloxy)-propanoic acid salt is used as the starting material. In certain embodiments, supra, for making crystalline forms of 2-amino-3-(2,6-diisopropylphenoxycarbonyloxy)-propanoic acid salt, the (R)-enantiomer of 2-amino-3-(2,6-diisopropylphenoxycarbonyloxy)-propanoic acid salt is used as the starting material.

Synthesis

2-Amino-3-(2,6-diisopropylphenoxycarbonyloxy)-propanoic acid (2), or pharmaceutically acceptable salts, or solvates thereof, may be prepared via the synthetic method illustrated in Scheme 2. Starting materials useful for preparing these compounds and intermediates thereof are commercially available or can be prepared by well-known synthetic methods (Harrison et al., "Compendium of Synthetic Organic Methods", Vols. 1-8 (John Wiley and Sons, 1971-1996); "Beilstein Handbook of Organic Chemistry," Beilstein Institute of Organic Chemistry, Frankfurt, Germany; Feiser et al., "Reagents for Organic Synthesis," Volumes 1-17, Wiley Interscience; Trost et al., "Comprehensive Organic Synthesis," Pergamon Press, 1991; "Theilheimer's Synthetic Methods of Organic Chemistry," Volumes 1-45, Karger, 1991; March, "Advanced Organic Chemistry," Wiley Interscience, 1991; Larock "Comprehensive Organic Transformations," VCH Publishers, 1989; Paquette, "Encyclopedia of Reagents for Organic Synthesis," John Wiley & Sons, 1995). Other methods for synthesis of compound (2) will be readily apparent to the skilled artisan. Accordingly, the method presented in Scheme 2 herein is illustrative rather than comprehensive.

Scheme 2

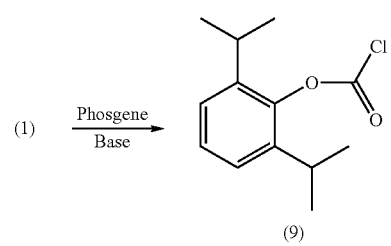

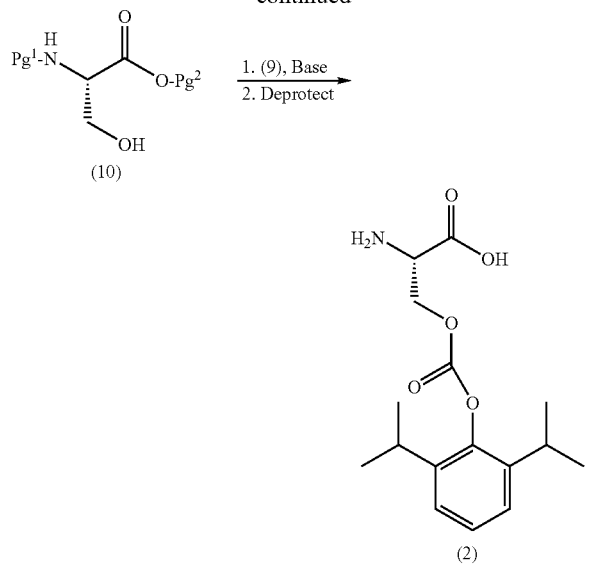

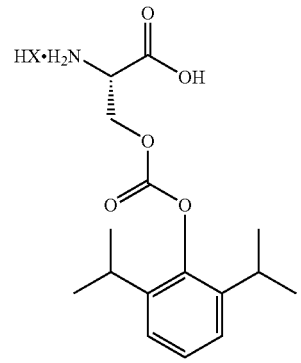

In certain embodiments, Pg$^1$ is Boc and Pg$^2$ is Bn, and the deprotection sequence outlined in Scheme 2 comprising hydrogenolysis and trifluoroacetic acid treatment affords the trifluoroacetate salt of (S)-2-amino-3-(2,6-diisopropylphenoxy-carbonyloxy)-propanoic acid, i.e., compound (8) (see Scheme 3):

Propofol can be converted to the chloroformate derivative (9) by treatment with phosgene (or an equivalent reagent) in the presence of a base such as N,N-dimethylaniline and a non-protic solvent such as toluene. Compound (9) can be reacted with an appropriately protected derivative of L-serine (10) (D-serine may be used to synthesize the enantiomer) in the presence of a base such as pyridine and a non-protic solvent such as dichloromethane, optionally in the presence of an acyl transfer catalyst such as 4-N,N-dimethylaminopyridine (DMAP). Both the amino and carboxyl groups in the serine derivative (10) can be masked with protecting groups (Pg$^1$ and Pg$^2$, respectively) that are amenable to removal under conditions compatible with stability of the target compound (2). Suitable protecting groups Pg$^1$ include tert-butoxycarbonyl (Boc) and carbobenzyloxy (CBz), which are removable under acidic and hydrogenolysis conditions, respectively. Suitable protecting groups Pg$^2$ include tert-butyl (tBu) and benzyl (Bn) esters, which are removable under acidic and hydrogenolysis conditions, respectively. In certain embodiments, Pg$^1$ is Boc and Pg$^2$ is Bn.

One of ordinary skill in the art will appreciate that 2-amino-3-(2,6-diisopropylphenoxycarbonyloxy)-propanoic acid (2) may exist as a zwitterionic species (i.e., as compound (3)) or may be readily converted to a protic acid addition salt (i.e., as compound (4), where X is an anionic moiety).

Scheme 3

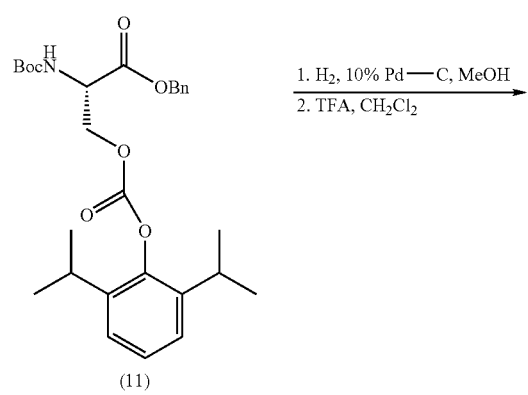

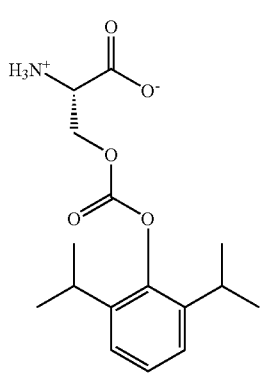

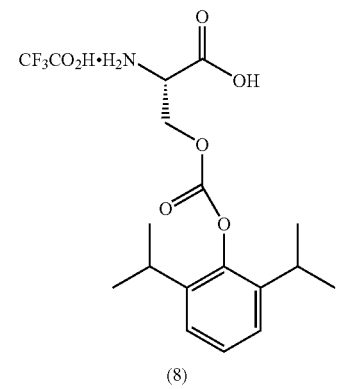

Compound (8) is isolated as a white solid after removal of solvent and addition of diethyl ether. After dissolution of (8) in water (or aqueous/organic mixtures), adjustment of the solution pH to ~7 (via addition of a weak base such as bicarbonate) results in precipitation of the zwitterion (3) as an amorphous white solid (see Scheme 4):

Scheme 4

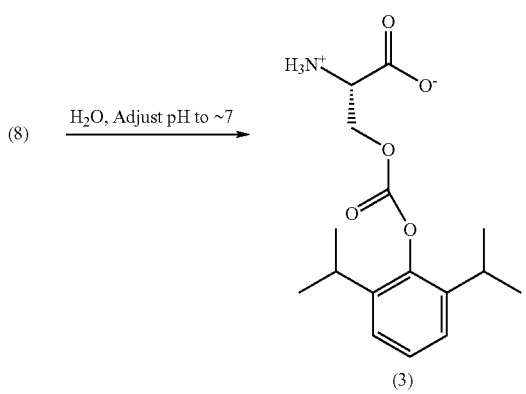

Zwitterion (3) can be converted to the corresponding protic acid addition salt (4) via dissolution in a solution of acid HX and either precipitation or removal of the solvent in vacuo. Thus dissolution in aqueous HCl or methanesulfonic acid affords (S)-2-amino-3-(2,6-diisopropylphenoxycarbonyloxy)-propanoic acid hydrochloride (6) and (S)-2-amino-3-(2,6-diisopropylphenoxycarbonyloxy)-propanoic acid mesylate (7), respectively, as illustrated in Scheme 5.

Scheme 5

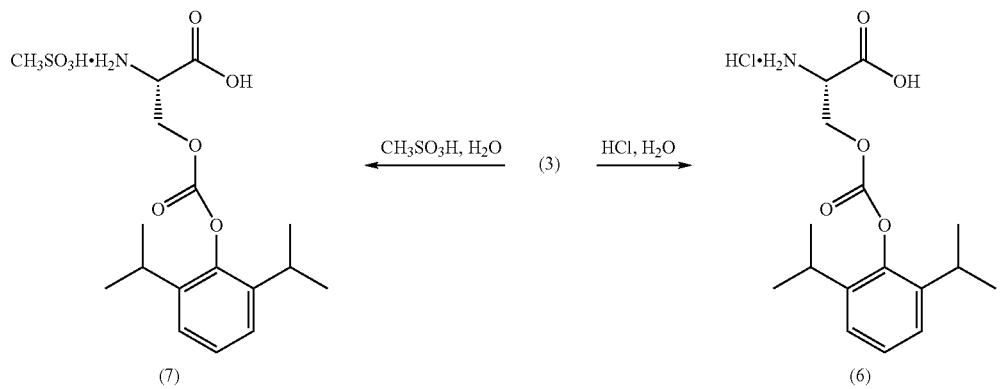

The skilled artisan will appreciate that the methods disclosed, supra, may be used to prepare enantiomerically pure (S)-2-amino-3-(2,6-diisopropylphenoxycarbonyloxy)-propanoic acid, enantiomerically pure (R)-2-amino-3-(2,6-diisopropylphenoxycarbonyloxy)-propanoic acid, or enantiomeric mixtures thereof including racemic mixtures, and pharmaceutically acceptable salts of any of the foregoing, and pharmaceutically acceptable solvates of any of the foregoing. The skilled artisan will also appreciate that 2-amino-3-(2,6-diisopropylphenoxycarbonyloxy)-propanoic acid can have various compositional and enantiomeric purities. In certain embodiments, 2-amino-3-(2,6-diisopropylphenoxycarbonyloxy)-propanoic acid can exhibit a compositional purity of at least about 90%, at least about 91%, at least about 92%, at least about 93%, at least about 94%, at least about 95%, at least about 96%, at least about 97%, at least about 98%, at least about 99%, and in certain embodiments, in excess of at least about 99%. In certain embodiments, 2-amino-3-(2,6-diisopropylphenoxycarbonyloxy)-propanoic acid can exhibit an enantiomeric purity of at least about 90%, at least about 91%, at least about 92%, at least about 93%, at least about 94%, at least about 95%, at least about 96%, at least about 97%, at least about 98%, at least about 99%, and in certain embodiments, in excess of at least about 99%.

Therapeutic/Prophylactic Uses and Methods of Administration

2-Amino-3-(2,6-diisopropylphenoxycarbonyloxy)-propanoic acid or pharmaceutically acceptable salts, or solvates thereof or crystalline forms thereof as disclosed herein, may be used to treat and/or prevent headache pain such as migraine in patients. The methods comprise administering to a patient a therapeutically effective amount of 2-amino-3-(2,6-diisopropylphenoxycarbonyloxy)-propanoic acid, or pharmaceutically acceptable salts, or solvates thereof, to treat and/or prevent headache pain such as migraine. In the therapeutic methods herein, a therapeutically effective amount of 2-amino-3-(2,6-diisopropylphenoxycarbonyloxy)-propanoic acid can be administered to a patient suffering from headache pain such as migraine. In the prophylactic methods herein, a therapeutically effective amount of 2-amino-3-(2,6-diisopropylphenoxycarbonyloxy)-propanoic acid can be administered to a patient at risk of developing headache pain.

In certain embodiments, 2-amino-3-(2,6-diisopropylphenoxycarbonyloxy)-propanoic acid can be administered orally to treat and/or prevent headache pain. However, in certain embodiments, 2-amino-3-(2,6-diisopropylphenoxycarbonyloxy)-propanoic acid can be administered parenterally (e.g., via inhalation or injection). In certain embodiments, 2-amino-3-(2,6-diisopropylphenoxycarbonyloxy)-propanoic acid can be administered in amounts from about 100 mg to about 4 g to treat or prevent headache pain such as migraine.

2-Amino-3-(2,6-diisopropylphenoxycarbonyloxy)-propanoic acid or pharmaceutically acceptable salts, or solvates thereof or crystalline forms thereof as disclosed herein, may also be used as anti-emetics and can be administered to patients at risk of vomiting and/or who are nauseous. For example, 2-amino-3-(2,6-diisopropylphenoxycarbonyloxy)-propanoic acid may be administered to patients that are being concurrently treated with various chemotherapy agents and/or surgical procedures, which induce nausea, in order to treat and/or prevent nausea and vomiting. In certain embodiments, a therapeutically effective amount of 2-amino-3-(2,6-diisopropylphenoxycarbonyloxy)-propanoic acid can be administered to a patient to treat and/or prevent nausea and vomiting. In certain embodiments, 2-amino-3-(2,6-diisopropylphenoxycarbonyloxy)-propanoic acid can be administered orally to treat and/or prevent nausea or vomiting. However, in certain embodiments, 2-amino-3-(2,6-diisopropylphenoxycarbonyloxy)-propanoic acid can be administered parenterally (e.g., via inhalation or injection to treat and/or prevent nausea or vomiting). In certain embodiments, 2-amino-3-(2,6-diisopropylphenoxycarbonyloxy)-propanoic acid can be administered in amounts from about 100 mg to about 4 g to treat and/or prevent nausea or vomiting.

2-Amino-3-(2,6-diisopropylphenoxycarbonyloxy)-propanoic acid or pharmaceutically acceptable salts, or solvates thereof or crystalline forms thereof as disclosed herein, may also be used as hypnotic agents to induce and/or maintain general anesthesia and/or as a sedative. In certain embodiments, a therapeutically effective amount of 2-amino-3-(2,6-diisopropylphenoxycarbonyloxy)-propanoic acid can be administered to a patient to induce hypnosis, anesthesia, and/or sedation.

In certain embodiments, 2-amino-3-(2,6-diisopropylphenoxycarbonyloxy)-propanoic acid can be administered intravenously when used as a general anesthetic. In certain embodiments, 2-amino-3-(2,6-diisopropylphenoxycarbonyloxy)-propanoic acid can be administered by inhalation. 2-Amino-3-(2,6-diisopropylphenoxycarbonyloxy)-propanoic acid may be formulated by methods used to formulate propofol, which are well known in the art. In certain embodiments, 2-amino-3-(2,6-diisopropylphenoxycarbonyloxy)-propanoic acid and pharmaceutically acceptable salts, or solvates thereof, and crystalline forms thereof that are water soluble may be formulated as an injectable aqueous solution, which contains significantly less emulsifiers or solubilizers than used in aqueous formulations of propofol, thereby avoiding discomfort at the site of injection.

In certain embodiments, 2-amino-3-(2,6-diisopropylphenoxycarbonyloxy)-propanoic acid can be administered orally in amounts from about 100 mg to about 4 g daily when used as a sedative (e.g., for the treatment of anxiety conditions, or for endoscopic or colonscopic procedures). However, in certain embodiments, 2-amino-3-(2,6-diisopropylphenoxycarbonyloxy)-propanoic acid may also be administered by inhalation, intravenously, or intramuscularly when used as a sedative.

2-Amino-3-(2,6-diisopropylphenoxycarbonyloxy)-propanoic acid or pharmaceutically acceptable salts, or solvates thereof, or crystalline forms thereof as disclosed herein, may be administered in similar amounts and in the same schedule as described in the art for propofol. In certain embodiments, dosage levels of these compounds for producing general anesthesia, maintaining anesthesia, and producing a sedative effect are as described in the art for propofol.

2-Amino-3-(2,6-diisopropylphenoxycarbonyloxy)-propanoic acid or pharmaceutically acceptable salts, or solvates thereof, or crystalline forms thereof as disclosed herein, may also be used to inhibit oxidation in biological materials. The methods include contacting the biological material with an effective amount of 2-amino-3-(2,6-diisopropylphenoxycarbonyloxy)-propanoic acid. In therapeutic methods herein, a therapeutically effective amount of 2-amino-3-(2,6-diisopropylphenoxycarbonyloxy)-propanoic acid can be administered to a patient suffering from a pathological condition treated by inhibition of oxidation. In prophylactic methods herein, a therapeutically effective amount of 2-amino-3-(2,6-diisopropylphenoxycarbonyloxy)-propanoic acid can be administered to a patient at risk of developing a disease as a result of exposure to oxidative stress. 2-Amino-3-(2,6-diisopropylphenoxycarbonyloxy)-propanoic acid may find particular use in preventing and/or treating oxidation in disorders of the central nervous system that involve an inflammatory component.

2-Amino-3-(2,6-diisopropylphenoxycarbonyloxy)-propanoic acid or pharmaceutically acceptable salts, or solvates thereof, or crystalline forms thereof as disclosed herein, may be used to treat or prevent mood disorders such as depression, or more particularly, depressive disorders, for example, single episodic or recurrent major depressive disorders, dysthymic disorders, depressive neurosis and neurotic depression, melancholic depression, including anorexia, weight loss, insomnia, early morning waking and psychomotor retardation, atypical depression or reactive depression, including increased appetite, hypersomnia, psychomotor agitation or irritability, seasonal affective disorder and pediatric depression; bipolar disorders or manic depression, such as bipolar I disorder, bipolar II disorder, and cyclothymic disorder; conduct disorder and disruptive behavior disorder; anxiety disorders, such as panic disorder with or without agoraphobia, agoraphobia without history of panic disorder, specific phobias, for example, specific animal phobias, social anxiety, social phobia, obsessive-compulsive disorder, stress disorders, including post-traumatic stress disorder and acute stress disorder, and generalized anxiety disorders; borderline personality disorder; schizophrenia and other psychotic disorders, for example, schizophreniform disorders, schizoaffective disorders, delusional disorders, brief psychotic disorders, shared psychotic disorders, psychotic disorders with delusions or hallucinations, psychotic episodes of anxiety, anxiety associated with psychosis, psychotic mood disorders such as severe major depressive disorder; mood disorders associated with psychotic disorders such as acute mania and depression associated with bipolar disorder, mood disorders associated with schizophrenia; and behavioral disturbances associated with mental retardation, autistic disorder, and conduct disorder.

2-Amino-3-(2,6-diisopropylphenoxycarbonyloxy)-propanoic acid or pharmaceutically acceptable salts, or solvates thereof, or crystalline forms thereof as disclosed herein, may be used to treat or prevent delirium, dementia, and amnestic and other cognitive or neurodegenerative disorders, such as Parkinson's disease (PD), Huntington's disease (HD), Alzheimer's disease, senile dementia, dementia of the Alzheimer's type, memory disorders, loss of executive function, vascular dementia, and other dementias, for example, due to HIV disease, head trauma, Parkinson's disease, Huntington's disease, Pick's disease, Friedrich's disease, Creutzfeldt-Jakob disease, or due to multiple etiologies; movement disorders such as akinesias, dyskinesias, including familial paroxysmal dyskinesias, spasticities, Tourette's syndrome, Scott syndrome, PALSYS and akinetic-rigid syndrome; extra-pyramidal movement disorders such as medication-induced movement disorders, for example, neuroleptic-induced Parkinsonism, neuroleptic malignant syndrome, neuroleptic-induced acute dystonia, neuroleptic-induced acute akathisia, neuroleptic-induced tardive dyskinesia and medication-induced postural tremor; chemical dependencies and addictions (e.g., dependencies on, or addictions to, alcohol, heroin, cocaine, benzodiazepines, nicotine, or phenobarbitol) and behavioral addictions such as an addiction to gambling; and ocular disorders such as glaucoma and ischemic retinopathy.

2-Amino-3-(2,6-diisopropylphenoxycarbonyloxy)-propanoic acid or pharmaceutically acceptable salts, or solvates thereof, or crystalline forms thereof as disclosed herein, may be used to treat or prevent movement disorders such as akinesias, dyskinesias, including familial paroxysmal dyskinesias, spasticities, Tourette's syndrome, Scott syndrome, PALSYS and akinetic-rigid syndrome; extra-pyramidal movement disorders such as medication-induced movement disorders, for example, neuroleptic-induced Parkinsonism, neuroleptic malignant syndrome, neuroleptic-induced acute dystonia, neuroleptic-induced acute akathisia, neuroleptic-induced tardive dyskinesia and medication-induced postural tremor.

2-Amino-3-(2,6-diisopropylphenoxycarbonyloxy)-propanoic acid or pharmaceutically acceptable salts, or solvates thereof, or crystalline forms thereof as disclosed herein, may be used to treat or prevent addictive disorders and withdrawal syndrome, chemical dependencies and addictions including dependencies on, or addictions to, alcohol, heroin, cocaine, benzodiazepines, psychoactive substances, nicotine, or phenobarbitol and behavioral addictions including addiction to gambling.

2-Amino-3-(2,6-diisopropylphenoxycarbonyloxy)-propanoic acid or pharmaceutically acceptable salts, or solvates thereof, or crystalline forms thereof as disclosed herein, may be used to treat and/or prevent neurodegenerative conditions of the nervous system, which include, but are not limited to, Friedrich's disease, Parkinson's disease, Alzheimer's disease, Huntington's disease, amyotrophic lateral sclerosis (ALS), multiple sclerosis (MS), and Pick's disease. In some embodiments, a therapeutically effective amount of 2-amino-3-(2,6-diisopropyl-phenoxycarbonyloxy)-propanoic acid (e.g., from about 100 mg to about 4 g daily) is orally administered to treat and/or prevent chronic neurodegenerative diseases.

2-Amino-3-(2,6-diisopropylphenoxycarbonyloxy)-propanoic acid or pharmaceutically acceptable salts, or solvates thereof, or crystalline forms thereof as disclosed herein, may also be used to treat and/or prevent trauma to the central nervous system such as, for example, skull fracture and its resulting edema, concussion, contusion, brain hemorrhages, shearing lesions, subdural and epidural hematoma, and spinal cord injury (e.g., mechanical injury due to compression or flexion of the spinal cord). In certain embodiments, 2-amino-3-(2,6-diisopropyl-phenoxycarbonyloxy)-propanoic acid is parenterally administered by intravenous injection or injection directly into the central nervous system (i.e., intrathecally (IT) or into the brain) to treat and/or prevent traumatic conditions of the central nervous system. In certain embodiments, a therapeutically effective amount of 2-amino-3-(2,6-diisopropylphenoxycarbonyloxy)-propanoic acid (e.g., from about 25 mg to about 500 mg IV or IM and from about 5 mg to about 100 mg IT) is administered to treat and/or prevent traumatic conditions of the central nervous system.

2-Amino-3-(2,6-diisopropylphenoxycarbonyloxy)-propanoic acid or pharmaceutically acceptable salts, or solvates thereof; or crystalline forms thereof as disclosed herein, may also be used as an anti-convulsive to treat and/or prevent seizures (e.g., epileptic seizures). Methods for treating and/or preventing convulsions can comprise administering a therapeutically effective amount of 2-amino-3-(2,6-diisopropylphenoxycarbonyloxy)-propanoic acid to a patient in need of such treatment. In some embodiments, 2-amino-3-(2,6-diisopropylphenoxycarbonyloxy)-propanoic acid is administered orally to treat and/or prevent convulsions. In certain embodiments, 2-amino-3-(2,6-diisopropylphenoxycarbonyloxy)-propanoic acid is parenterally administered to treat and/or prevent convulsions. In certain embodiments, 2-amino-3-(2, 6-diisopropylphenoxycarbonyloxy)-propanoic acid is administered in amounts from about 100 mg to about 4 g daily to treat and/or prevent convulsions.

2-Amino-3-(2,6-diisopropylphenoxycarbonyloxy)-propanoic acid or pharmaceutically acceptable salts, or solvates thereof, or crystalline forms thereof as disclosed herein, may also be used as anti-depressants to treat and/or prevent mood disorders such as depression. Methods for treating and/or preventing depression can comprise administering a therapeutically effective amount of 2-amino-3-(2,6-diisopropylphenoxycarbonyloxy)-propanoic acid to a patient in need of such treatment. In certain embodiments, 2-amino-3-(2,6-diisopropylphenoxycarbonyloxy)-propanoic acid can be administered orally to treat and/or prevent depression. In certain embodiments, 2-amino-3-(2,6-diisopropylphenoxycarbonyloxy)-propanoic acid is parenterally administered to treat and/or prevent depression. In certain embodiments, 2-amino-3-(2,6-diisopropylphenoxycarbonyloxy)-propanoic acid can be administered in amounts from about 100 mg to about 4 g daily to treat and/or prevent depression.

When used to treat and/or prevent the above disease or disorders 2-amino-3-(2,6-diisopropylphenoxycarbonyloxy)-propanoic acid or pharmaceutically acceptable salts, or solvates thereof, or crystalline forms thereof as disclosed herein, may be administered or applied singly, or in combination with other agents. The compounds and/or pharmaceutical compositions thereof may also be administered or applied singly, or in combination with other pharmaceutically active agents.

Provided herein are methods of treatment and prophylaxis by administering to a patient a therapeutically effective amount of 2-amino-3-(2,6-diisopropyl-phenoxycarbonyloxy)-propanoic acid or pharmaceutically acceptable salts, or solvates thereof, or crystalline forms thereof as disclosed herein. The patient may be an animal, in certain embodiments a mammal, and in certain embodiments a human.

2-Amino-3-(2,6-diisopropylphenoxycarbonyloxy)-propanoic acid or pharmaceutically acceptable salts, or solvates thereof, or crystalline forms thereof as disclosed herein, and/or pharmaceutical compositions thereof can be administered orally. 2-Amino-3-(2,6-diisopropylphenoxycarbonyloxy)-propanoic acid and/or pharmaceutical compositions thereof may also be administered by any other convenient route, for example, by infusion or bolus injection, by absorption through epithelial or mucocutaneous linings (e.g., oral mucosa, rectal, and intestinal mucosa, etc.). Administration can be systemic or local. Various delivery systems are known, (e.g., encapsulation in liposomes, microparticles, microcapsules, capsules, etc.) that can be used to administer a compound and/or pharmaceutical composition. Methods of administration include, but are not limited to, intradermal, intramuscular, intraperitoneal, intravenous, subcutaneous, intranasal, epidural, oral, sublingual, intranasal, intracerebral, intravaginal, transdermal, rectally, inhalation, or topically, particularly to the ears, nose, eyes, or skin.

In certain embodiments, it may be desirable to introduce 2-amino-3-(2,6-diisopropylphenoxycarbonyloxy)-propanoic acid and/or pharmaceutical compositions thereof into the central nervous system by any suitable route, including intraventricular, intrathecal, and epidural injection. Intraventricular injection may be facilitated by use of an intraventricular catheter, for example, attached to a reservoir, such as an Ommaya reservoir.

In certain embodiments, 2-amino-3-(2,6-diisopropylphenoxycarbonyloxy)-propanoic acid and/or pharmaceutical compositions thereof can be delivered via sustained release systems, can be oral sustained release systems. In certain embodiments, a pump may be used (Langer, supra; Sefton, *CRC Crit. Ref Biomed Eng.* 1987, 14, 201; and Saudek et al., *N. Engl. J Med.* 1989, 321, 574).

In still other embodiments, polymeric materials can be used (see "Medical Applications of Controlled Release," Langer and Wise (eds.), CRC Pres., Boca Raton, Fla. (1974); "Controlled Drug Bioavailability," Drug Product Design and Performance, Smolen and Ball (eds.), Wiley, New York (1984); Langer et al., *J Macromol. Sci. Rev. Macromol Chem.*

1983, 23, 61; Levy et al., *Science* 1985, 228, 190; During et al., *Ann. Neurol.* 1989, 25, 351; and Howard et al., *J. Neurosurg.* 1989, 71, 105).

In certain embodiments, polymeric materials can be used for oral sustained release delivery. Polymers include, for example, sodium carboxymethylcellulose, hydroxypropylcellulose, hydroxypropylmethylcellulose, and hydroxyethylcellulose. Other cellulose ethers have been described (Alderman, *Int. J. Pharm. Tech. & Prod. Mfr.* 1984, 5(3), 1-9). Factors affecting drug release are well known to the skilled artisan and have been described in the art (Bamba et al., *Int. J. Pharm.* 1979, 2, 307).

In certain embodiments, enteric-coated preparations can be used for oral sustained release administration. Coating materials include, for example, polymers with a pH-dependent solubility (i.e., pH-controlled release), polymers with a slow or pH-dependent rate of swelling, dissolution or erosion (i.e., time-controlled release), polymers that are degraded by enzymes (i.e., enzyme-controlled release), and polymers that form firm layers that are destroyed by an increase in pressure (i.e., pressure-controlled release).

In certain embodiments, osmotic delivery systems can be used for oral sustained release administration (Verma et al., *Drug Dev. Ind. Pharm.* 2000, 26, 695-708). In certain embodiments, OROS™ osmotic devices can be used for oral sustained release delivery devices (Theeuwes et al., U.S. Pat. No. 3,845,770; Theeuwes et al., U.S. Pat. No. 3,916,899).

For administration by inhalation, 2-amino-3-(2,6-diisopropylphenoxy-carbonyloxy)-propanoic acid may be conveniently delivered to the lung by a number of different devices. For example, a Metered Dose Inhaler (MDI), which utilizes canisters that contain a suitable low boiling propellant, e.g., dichlorodifluoromethane, trichlorofluoromethane, dichlorotetrafluoroethane, carbon dioxide, or other suitable gas may be used to deliver compounds directly to the lung.

Alternatively, a Dry Powder Inhaler (DPI) device may be used to administer 2-amino-3-(2,6-diisopropylphenoxycarbonyloxy)-propanoic acid to the lung (See, e.g., Raleigh et al., *Proc. Amer. Assoc. Cancer Research Annual Meeting* 1999, 40, 397). DPI devices typically use a mechanism such as a burst of gas to create a cloud of dry powder inside a container, which may then be inhaled by the patient and are well known in the art, may be purchased from a number of commercial sources. A popular variation is the multiple-dose DPI (MD-DPI) system, which allows for the delivery of more than one therapeutic dose. For example, capsules and cartridges of gelatin for use in an inhaler or insufflator may be formulated containing a powder mix of a compound and a suitable powder base such as lactose or starch for these systems.

Another type of device that may be used to deliver 2-amino-3-(2,6-diisopropylphenoxycarbonyloxy)-propanoic acid to the lung is a liquid spray device supplied, for example, by Aradigm Corporation, Hayward, Calif. Liquid spray systems use extremely small nozzle holes to aerosolize liquid drug formulations that may then be directly inhaled into the lung.

In certain embodiments, a nebulizer device is used to deliver 2-amino-3-(2,6-diisopropylphenoxycarbonyloxy)-propanoic acid to the lung. Nebulizers create aerosols from liquid drug formulations by using, for example, ultrasonic energy to form fine particles that may be readily inhaled (e.g., Verschoyle et al., *British J. Cancer* 1999, 80, Suppl. 2, 96; Armer et al., U.S. Pat. No. 5,954,047; van der Linden et al., U.S. Pat. No. 5,950,619; and van der Linden et al., U.S. Pat. No. 5,970,974).

In certain embodiments, an electrohydrodynamic (EHD) aerosol device is used to deliver 2-amino-3-(2,6-diisopropylphenoxycarbonyloxy)-propanoic acid to the lung. EHD aerosol devices use electrical energy to aerosolize liquid drug solutions or suspensions (see e.g., Noakes et al., U.S. Pat. No. 4,765,539; Coffee, U.S. Pat. No. 4,962,885; Coffee, International Publication No., WO 94/12285; Coffee, International Publication No., WO 94/14543; Coffee, International Publication No., WO 95/26234; Coffee, International Publication No., WO 95/26235; and Coffee, International Publication No., WO 95/32807). The electrochemical properties of 2-amino-3-(2,6-diisopropylphenoxycarbonyloxy)-propanoic acid may be important parameters to optimize when delivering the compound to the lung with an EHD aerosol device, and such optimization is routinely performed by one of skill in the art. EHD aerosol devices may more efficiently deliver drugs to the lung than existing pulmonary delivery technologies. Other methods of intra-pulmonary delivery of a compound are known to the skilled artisan.

2-Amino-3-(2,6-diisopropylphenoxycarbonyloxy)-propanoic acid or pharmaceutically acceptable salts, or solvates thereof or crystalline forms thereof as disclosed herein, and/or pharmaceutical compositions thereof can provide therapeutic or prophylactic levels of propofol upon in vivo administration to a patient. The serine promoiety of the compounds may be cleaved either chemically and/or enzymatically to release the drug, propofol. One or more enzymes present in the stomach, intestinal lumen, intestinal tissue, blood, liver, brain, or any other suitable tissue of a mammal may enzymatically cleave the promoiety of the administered compounds. For example, the promoiety of 2-amino-3-(2,6-diisopropylphenoxycarbonyloxy)-propanoic acid may be cleaved prior to absorption by the gastrointestinal tract (e.g., within the stomach or intestinal lumen) and/or after absorption by the gastrointestinal tract (e.g., in intestinal tissue, blood, liver, or other suitable tissue of a mammal). In certain embodiments, propofol remains conjugated to the serine promoiety during transit across the intestinal mucosal barrier to provide protection from presystemic metabolism. In certain embodiments, 2-amino-3-(2,6-diisopropyl-phenoxycarbonyloxy)-propanoic acid is essentially not metabolized to propofol within enterocytes, but is metabolized to the parent drug within the systemic circulation. Cleavage of the promoiety of 2-amino-3-(2,6-diisopropylphenoxycarbonyloxy)-propanoic acid after absorption by the gastrointestinal tract may allow these prodrugs to be absorbed into the systemic circulation either by active transport, passive diffusion, or by a combination of both active and passive processes.

Pharmaceutical Compositions

The present pharmaceutical compositions contain a therapeutically effective amount of 2-amino-3-(2,6-diisopropylphenoxycarbonyloxy)-propanoic acid or pharmaceutically acceptable salts, or solvates thereof, or crystalline forms thereof as disclosed herein, in certain embodiments in purified form, together with a suitable amount of a pharmaceutically acceptable vehicle, so as to provide the form for proper administration to a patient. When administered intravenously to a patient, 2-amino-3-(2,6-diisopropylphenoxycarbonyloxy)-propanoic acid and pharmaceutically acceptable vehicles can be sterile. Water is a preferred vehicle when 2-amino-3-(2,6-diisopropylphenoxycarbonyloxy)-propanoic acid is administered intravenously. Saline solutions, aqueous dextrose solutions, and glycerol solutions can also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The present compositions, if desired, can also contain minor amounts of wetting or emulsifying agents, or pH buffering agents. In addition, auxiliary, stabilizing, thickening, lubricating, and coloring agents may be used.

Pharmaceutical compositions comprising 2-amino-3-(2,6-diisopropylphenoxy-carbonyloxy)-propanoic acid or pharmaceutically acceptable salts, or solvates thereof or crystalline forms thereof as disclosed herein, may be manufactured by means of conventional mixing, dissolving, granulating, dragee-making, levigating, emulsifying, encapsulating, entrapping, or lyophilizing processes. Pharmaceutical compositions may be formulated in conventional manner using one or more physiologically acceptable carriers, diluents, excipients, or auxiliaries, which facilitate processing of compounds into preparations that can be used pharmaceutically. Proper formulation is dependent upon the route of administration chosen.

The present pharmaceutical compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In some embodiments, the pharmaceutically acceptable vehicle is a capsule (see e.g., Grosswald et al., U.S. Pat. No. 5,698,155). Other examples of suitable pharmaceutical vehicles have been described in the art (see Remington's Pharmaceutical Sciences, Philadelphia College of Pharmacy and Science, 19th Edition, 1995). Preferred pharmaceutical compositions are formulated for oral delivery.

Pharmaceutical compositions for oral delivery may be in the form of tablets, lozenges, aqueous or oily suspensions, granules, powders, emulsions, capsules, syrups, or elixirs, for example. Orally administered pharmaceutical compositions may contain one or more optional agents, for example, sweetening agents such as fructose, aspartame or saccharin, flavoring agents such as peppermint, oil of wintergreen, or cherry coloring agents and preserving agents, to provide a pharmaceutically palatable preparation. Moreover, where in tablet or pill form, the pharmaceutical compositions may be coated to delay disintegration and absorption in the gastrointestinal tract, thereby providing a sustained action over an extended period of time. Selectively permeable membranes surrounding an osmotically active driving compound are also suitable for orally administered compounds and pharmaceutical compositions. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate may also be used. Oral pharmaceutical compositions can include standard vehicles such as mannitol, lactose, starch, magnesium stearate, sodium saccharine, cellulose, magnesium carbonate, etc. Such vehicles can be of pharmaceutical grade.

For oral liquid preparations such as, for example, suspensions, elixirs and solutions; suitable carriers, excipients, or diluents include water, saline, alkyleneglycols (e.g., propylene glycol), polyalkylene glycols (e.g., polyethylene glycol) oils, alcohols, slightly acidic buffers from about pH 4 to about pH 6 (e.g., acetate, citrate, ascorbate from about 5 mM to about 50 mM), etc. Additionally, flavoring agents, preservatives, coloring agents, bile salts, acylcarnitines, and the like may be added.

In addition to the formulations disclosed previously, 2-amino-3-(2,6-diisopropylphenoxycarbonyloxy)-propanoic acid or pharmaceutically acceptable salts, or solvates thereof, or crystalline forms thereof as disclosed herein, may also be formulated as a depot preparation. Such long acting formulations may be administered by implantation (for example subcutaneously or intramuscularly) or by intramuscular injection. Thus, for example, 2-amino-3-(2,6-diisopropylphenoxy-carbonyloxy)-propanoic acid may be formulated with suitable polymeric or hydrophobic materials (for example as an emulsion in an acceptable oil), ion exchange resins, or as sparingly soluble derivatives, for example, as a sparingly soluble salt.

Liquid drug formulations suitable for use with nebulizers and liquid spray devices and EHD aerosol devices can include 2-amino-3-(2,6-diisopropyl-phenoxycarbonyloxy)-propanoic acid with a pharmaceutically acceptable carrier. In certain embodiments, the pharmaceutically acceptable carrier is a liquid such as alcohol, water, polyethylene glycol, or a perfluorocarbon. Optionally, another material may be added to alter the aerosol properties of the solution or suspension of 2-amino-3-(2,6-diisopropylphenoxycarbonyloxy)-propanoic acid. In certain embodiments, this material is liquid such as an alcohol, glycol, polyglycol, or a fatty acid. Other methods of formulating liquid drug solutions or suspension suitable for use in aerosol devices are known to those of skill in the art (e.g., Biesalski, U.S. Pat. No. 5,112,598; Biesalski, U.S. Pat. No. 5,556,611).

Combination Therapy

In certain embodiments, 2-amino-3-(2,6-diisopropylphenoxycarbonyloxy)-propanoic acid or pharmaceutically acceptable salts, or solvates thereof or crystalline forms thereof as disclosed herein, can be used in combination therapy with at least one other therapeutic agent. 2-Amino-3-(2,6-diisopropylphenoxycarbonyloxy)-propanoic acid and the at least one other therapeutic agent can act additively or, in certain embodiments, synergistically. In certain embodiments, 2-amino-3-(2,6-diisopropylphenoxycarbonyloxy)-propanoic acid can be administered concurrently with the administration of another therapeutic agent, such as for example, another sedative, hypnotic agent, or anesthetic agent (e.g., propofol). In certain embodiments, 2-amino-3-(2, 6-diisopropylphenoxycarbonyloxy)-propanoic acid or pharmaceutically acceptable salts, or solvates thereof or crystalline forms can be administered prior or subsequent to administration of another therapeutic agent, such as, for example, another sedative, hypnotic agent, or anesthetic agent, (e.g., propofol).

Pharmaceutical compositions of the present disclosure can include, in addition to one or more compounds of the present disclosure, one or more therapeutic agents effective for treating the same or different disease, disorder, or condition.

Methods of the present disclosure include administration of one or more compounds or pharmaceutical compositions of the present disclosure and one or more other therapeutic agents, provided that the combined administration does not inhibit the therapeutic efficacy of the one or more compounds of the present disclosure and/or does not produce adverse combination effects.

Compounds of the present disclosure and another therapeutic agent or agents can act additively or synergistically. In certain embodiments, compositions of the present disclosure can be administered concurrently with the administration of another therapeutic agent, which can be part of the same pharmaceutical composition as, or in a different composition from, that containing the compounds of the present disclosure. In certain embodiments, compounds of the present disclosure can be administered prior or subsequent to administration of another therapeutic agent. In certain embodiments of combination therapy, the combination therapy comprises alternating between administering a composition of the present disclosure and a composition comprising another therapeutic agent, e.g., to minimize adverse side effects associated with a particular drug. When a compound of the present disclosure is administered concurrently with another therapeutic agent that potentially can produce adverse side effects including, but not limited to, toxicity, the therapeutic agent can advantageously be administered at a dose that falls below the threshold at which the adverse side effect is elicited.

In certain embodiments, a drug can further comprise substances to enhance, modulate and/or control release, bioavailability, therapeutic efficacy, therapeutic potency, stability, and the like. For example, to enhance therapeutic efficacy a drug can be co-administered with one or more active agents to increase the absorption or diffusion of the drug through the gastrointestinal tract, or to inhibit degradation of the drug in the systemic circulation. In certain embodiments, a drug can be co-administered with active agents having pharmacological effects that enhance the therapeutic efficacy of the drug.

In certain embodiments, compounds or pharmaceutical compositions of the present disclosure include, or can be administered to a patient together with, another compound for treating pain including anxiolytics, drugs for treating headache pain such as migraine, nonsteroidal anti-inflammatory drugs, opioid drugs, analgesic drugs, and combinations of any of the foregoing.

Examples of anxiolytics include alprazolam, bromazepam, oxazepam, buspirone, hydroxyzine, mecloqualone, medetomidine, metomidate, adinazolam, chlordiazepoxide, clobenzepam, flurazepam, lorazepam, loprazolam, midazolam, alpidem, alseroxlon, amphenidone, azacyclonol, bromisovalum, captodiamine, capuride, carbcloral, carbromal, chloral betaine, enciprazine, flesinoxan, ipsapiraone, lesopitron, loxapine, methaqualone, methprylon, propanolol, tandospirone, trazadone, zopiclone, and zolpidem.

Examples of drugs for treating migraine headache include almotriptan, alperopride, codeine, dihydroergotamine, ergotamine, eletriptan, frovatriptan, isometheptene, lidocaine, lisuride, metoclopramide, naratriptan, oxycodone, propoxyphene, rizatriptan, sumatriptan, tolfenamic acid, zolmitriptan, amitriptyline, atenolol, clonidine, cyproheptadine, diltiazem, doxepin, fluoxetine, lisinopril, methysergide, metoprolol, nadolol, nortriptyline, paroxetine, pizotifen, pizotyline, propanolol, protriptyline, sertraline, timolol, and verapamil.

Examples of nonsteroidal anti-inflammatory drugs include aceclofenac, acetaminophen, alminoprofen, amfenac, aminopropylon, amixetrine, aspirin, benoxaprofen, bromfenac, bufexamac, carprofen, celecoxib, choline, salicylate, cinchophen, cinmetacin, clopriac, clometacin, diclofenac, diflunisal, etodolac, fenoprofen, flurbiprofen, ibuprofen, indomethacin, indoprofen, ketoprofen, ketorolac, mazipredone, meclofenamate, nabumetone, naproxen, parecoxib, piroxicam, pirprofen, rofecoxib, sulindac, tolfenamate, tolmetin, and valdecoxib.

Examples of opioid drugs include alfentanil, allylprodine, alphaprodine, anileridine, benzylmorphine, bezitramide, buprenorphine, butorphanol, carbiphene, cipramadol, clonitazene, codeine, dextromoramide, dextropropoxyphene, diamorphine, dihydrocodeine, diphenoxylate, dipipanone, fentanyl, hydromorphone, L-alpha acetyl methadol, lofentanil, levorphanol, meperidine, methadone, meptazinol, metopon, morphine, nalbuphine, nalorphine, oxycodone, papavereturn, pethidine, pentazocine, phenazocine, remifentanil, sufentanil, and tramadol.

Examples of other analgesic drugs include apazone, benzpiperylon, benzydramine, caffeine, clonixin, ethoheptazine, flupirtine, nefopam, orphenadrine, propacetamol, and propoxyphene In certain embodiments, compounds or pharmaceutical compositions of the present disclosure can include, or can be administered to a patient together with, another compound for treating emesis. Examples of antiemetics include alizapride, azasetron, benzquinamide, bromopride, buclizine, chlorpromazine, cinnarizine, clebopride, cyclizine, diphenhydramine, diphenidol, dolasetron, droperidol, granisetron, hyoscine, lorazepam, dronabinol, metoclopramide, metopimazine, ondansetron, perphenazine, promethazine, prochlorperazine, scopolamine, triethylperazine, trifluoperazine, triflupromazine, trimethobenzamide, tropisetron, domperidone, and palonosetron.

In certain embodiments, compounds or pharmaceutical compositions of the present disclosure can include, or can be administered to a patient together with, another compound for treating a neurodegenerative disorder including epilepsy, Friedrich's disease, Parkinson's disease, Alzheimer's disease, Huntington's disease, amyotrophic lateral sclerosis (ALS), multiple sclerosis (MS), and Pick's disease.

Examples of drugs for treating epilepsy include GABA analogs, tiagabine, vigabatrin; barbiturates such as pentobarbital; benzodiazepines such as clonazepam; hydantoins such as phenyloin; phenyltriazines such as lamotrigine; and other anticonvulsants such as carbamazepine, topiramate, valproic acid, and zonisamide.

Examples of drugs for treating Friedrich's disease (e.g., ataxia) include antiepileptics such as carbamazepine, and valproate; antiseizure medications such as primidone and gabapentin; beta-blockers such as propranolol; dopamine agonists such as bromocriptine and pergolide; and tranquilizers including benzodiazepines such as diazepam and clonazepam.

Examples of antiparkisonian drugs include amantadine, baclofen, biperiden, benztropine, orphenadrine, procyclidine, trihexyphenidyl, levodopa, carbidopa, andropinirole, apomorphine, benserazide, bromocriptine, budipine, cabergoline, eliprodil, eptastigmine, ergoline, galanthamine, lazabemide, lisuride, mazindol, memantine, mofegiline, pergolide, piribedil, pramipexole, propentofylline, rasagiline, remacemide, ropinerole, selegiline, spheramine, terguride, entacapone, and tolcapone.

Examples of drugs for treating Alzheimer's disease management include donepezil, galanthamine, and tacrin.

Examples of drugs for treating Huntington's disease include antipsychotics such as haloperidol, chlorpromazine, and olanzapine; antidepressants such as fluoxetine, sertraline hydrochloride, and nortriptyline; tranquilizers such as benzodiazepines, paroxetine, venlafaxin, and beta-blockers; mood-stabilizers such as lithium, valproate, and carbamazepine; and Botulinum toxin.

Examples of drugs for treating ALS include riluzole, baclofen, tizanadine, nonsteroidal anti-inflammatory drugs such as ibuprofen or naproxen, and tramadol.

Examples of drugs for multiple sclerosis management include bencyclane, methylprednisolone, mitoxantrone, and prednisolone.

In certain embodiments, compounds or pharmaceutical compositions of the present disclosure can include, or can be administered to a patient together with, another compound for treating depression. Examples of antidepressants include amitriptyline, amoxapine, benmoxine, butriptyline, clomipramine, desipramine, dosulepin, doxepin, imipramine, kitanserin, lofepramine, medifoxamine, mianserin, maprotoline, mirtazapine, nortriptyline, protriptyline, trimipramine, venlafaxine, viloxazine, citalopram, cotinine, duloxetine, fluoxetine, fluvoxamine, milnacipran, nisoxetine, paroxetine, reboxetine, sertraline, tianeptine, acetaphenazine, binedaline, brofaromine, cericlamine, clovoxamine, iproniazid, isocarboxazid, moclobemide, phenyhydrazine, phenelzine, selegiline, sibutramine, tranylcypromine, ademetionine, adrafinil, amesergide, amisulpride, amperozide, benactyzine, bupropion, caroxazone, gepirone, idazoxan, metralindole, milnacipran, minaprine, nefazodone, nomifensine, ritanserin, roxindole, S-adenosylmethionine, escitalopram, tofenacin, trazodone, tryptophan, and zalospirone.

EXAMPLES

The following examples describe in detail preparation of the S enantiomer of 2-amino-3-(2,6-diisopropylphenoxycarbonyloxy)-propanoic acid (2), and pharmaceutically acceptable salts, or solvates thereof. It will be apparent to those skilled in the art that many modifications, both to materials and methods, may be practiced without departing from the scope of the disclosure.

In the examples below, the following abbreviations have the following meanings. If an abbreviation is not defined, it has its generally accepted meaning.

| | |
|---|---|
| Boc = | tert-butyloxycarbonyl |
| Cbz = | carbobenzyloxy |
| DMAP = | 4-N,N-dimethylaminopyridine |
| g = | gram |
| h = | hour |
| kg = | kilogram |
| kV = | kilovolt |
| L = | liter |
| LC/MS = | liquid chromatography/mass spectroscopy |
| M = | molar |
| min = | minute |
| mA = | milliamp |
| mg = | milligram |
| mL = | milliliter |
| mm = | millimeter |
| mmol = | millimoles |
| µg = | microgram |
| µL = | microliter |
| µm = | micrometer |
| mM = | millimolar |
| µM = | micromolar |
| v/v = | volume to volume |

Example 1

(S)-2-Amino-3-(2,6-Diisopropylphenoxycarbonyloxy)-Propanoic Acid Trifluoroacetate (8)

Step 1: 2,6-Bis(isopropyl)phenoxycarbonyl chloride (9)

To a cooled (0° C.) solution of propofol (20.0 g, 112 mmol) in toluene (40 mL) was added phosgene (82 mL, 20% in toluene) under a nitrogen atmosphere. The reaction mixture was stirred for 5 min, and then N,N-dimethylaniline (15 mL, 118 mmol) was added dropwise. The mixture was allowed to warm to room temperature slowly and stirred for 14 h. The suspended mixture was then filtered. The filtrate was collected and the solvent was removed in vacuo. The remaining crude product (9) was carried to the next step without further purification. $^1$H-NMR (400 MHz, CDCl$_3$): δ 7.18-7.29 (m, 3H), 3.00-3.07 (m, 2H), 1.25-1.27 (d, J=6.8 Hz, 12H).

Step 2: Benzyl (S)-2-N-(tert-Butoxycarbonylamino)-3-(2,6-Diisopropylphenoxycarbonyloxy)-Propanoate (11)

To an ice cold solution of (S)-Boc-Ser-OBn (12.25 g, 41.5 mmol) in dichloromethane (100 mL) was added pyridine (4.0 mL, 49.4 mmol) and 4-(dimethylamino)pyridine (0.5 g, 4.0 mmol) followed by compound (9) (16 mL, 3.0 M in dichloromethane). The resulting mixture was allowed to warm to room temperature and stirred for 12 h. The mixture was then diluted with diethyl ether (150 mL) and washed with 10% aqueous citric acid solution (2×30 mL), dried over MgSO$_4$, filtered and concentrated in vacuo. The crude product (11) was carried to the next step without further purification. $^1$H-NMR (400 MHz, CD$_3$OD): δ 7.30-7.37 (m, 5H), 7.14-7.20 (m, 3H), 5.19 (s, 2H), 4.52-4.57 (m, 2H), 2.96-3.00 (m, 2H), 1.44 (s, 9H), 1.16-1.18 (d, J=6.8 Hz, 12H).

Step 3: (S)-2-N-(tert-Butoxycarbonylamino)-3-(2,6-Diisopropylphenoxycarbonyloxy)-Propanoic Acid (12)

To a flask containing 500 mg of 10% Pd—C was added a solution of compound (11) (5.0 g, 10.0 mmol) in MeOH (200 mL) under nitrogen. The resulting mixture was degassed three times, after which hydrogen was introduced via a balloon apparatus. The suspended mixture was allowed to stir vigorously for 4 h. The reaction mixture was filtered through a pad of celite and concentrated in vacuo to arrive at the title compound (12), which was used in subsequent reactions without further purification. $^1$H-NMR (400 MHz, CD$_3$OD): δ 7.14-7.22 (m, 3H), 4.51-4.59 (m, 2H), 2.98-3.02 (m, 2H), 1.46 (s, 9H), 1.18-1.19 (d, J=6.4 Hz, 12H).

Step 4: (S)-2-Amino-3-(2,6-Diisopropylphenoxycarbonyloxy)-Propanoic Acid Trifluoroacetate (8)

The crude compound (12) from above was dissolved in dichloromethane (60 mL) and treated with trifluoroacetic acid (20 mL). The resulting mixture was stirred at room temperature for 3 h. The solvent was removed in vacuo and the crude residue was diluted with diethyl ether (80 mL). After standing at room temperature for 2 min, a white precipitate formed. The mixture was then filtered and the white solid was rinsed with diethyl ether and collected to afford 2.05 g of the title compound (8). $^1$H-NMR (400 MHz, CD$_3$OD): δ 7.16-7.24 (m, 3H), 4.79-4.83 (dd, J=12.0, 4.8 Hz, 1H), 4.58-4.62 (dd, J=12.4 Hz, 2.8 Hz, 1H), 4.45 (t, J=3.2 Hz), 2.99-3.03 (m, 2H), 1.18-1.19 (d, J=7.2 Hz, 12H). MS (ESI) m/z 310.2 (M+H)$^+$.

Example 2

(S)-2-Amino-3-(2,6-Diisopropylphenoxycarbonyloxy)-Propanoic Acid (3)

To a stirred solution of compound (8) in H$_2$O and MeCN (20/1 v/v) was added a saturated aqueous sodium bicarbonate solution dropwise. The pH of this reaction mixture was monitored closely and the desired product precipitated as a white solid after the pH was adjusted to 7. The mixture was filtered and the title compound (3) was collected and dried in vacuo. $^1$H-NMR (400 MHz, CDCl$_3$): δ 7.15-7.22 (m, 3H), 4.64-4.68 (dd, J=11.6, 3.2 Hz, 1H), 4.55-4.60 (dd, J=11.6, 6.8 Hz, 1H), 3.28-3.30 (dd, J=6.8, 3.2 Hz, 1H), 2.99-3.04 (m, 2H), 1.18-1.19 (d, J=6.4 Hz, 12H). MS (ESI) m/z 310.3 (M+H)$^+$.

Example 3

Preparation of Crystalline (S)-2-Amino-3-(2,6-Diisopropylphenoxy-carbonyloxy)-Propanoic Acid Hydrochloride (6)

The hydrochloride salt of (S)-2-amino-3-(2,6-diisopropylphenoxy-carbonyloxy)-propanoic acid was prepared by dissolving compound (3) in excess aqueous 1 N hydrochloric acid solution, freezing and then lyophilizing the solution to afford the desired product as an amorphous white solid.

The hydrochloride (3.42 g, 9.89 mmol) was crystallized by dissolution in a mixture of ethanol and toluene (1/10 v/v, 110 mL) at 80° C. and the mixture allowed to cool to room temperature. Large needle-like crystals started to form after standing at room temperature for 48 h. The solution was filtered after standing for 7 days at room temperature. The product (6) was isolated as a white crystalline solid (2.7 g, 79% yield). $^1$H-NMR (400 MHz, CD$_3$OD): δ 7.16-7.24 (m, 3H), 4.81-4.85 (dd, J=12.4, 4.4 Hz, 1H), 4.59-4.63 (dd, J=12.0 Hz, 3.2 Hz, 1H), 4.45-4.49 (dd, J=4.4, 2.8 Hz, 1H), 2.98-3.02 (m, 2H), 1.18-1.19 (d, J=7.2 Hz, 12H). MS (ESI) m/z 310.3 (M+H)$^+$. Melting point: 188.1-189.1° C. There was no degradation of compound (6) as a solid or as an aqueous solution at room temperature after three months as determined by LC/MS. The solubility of compound (6) was determined to be 7.58 mg/mL in water, and 8.18 mg/mL in phosphate buffered saline (PBS).

Example 4

Preparation of Crystalline (S)-2-Amino-3-(2,6-Diisopropylphenoxy-carbonyloxy)-Propanoic Acid Mesylate (7)

To a suspension of compound (3) (4.44 g, 14.3 mmol) in H$_2$O (100 mL) was added methanesulfonic acid (0.93 mL, 14.3 mmol). The resulting mixture was stirred at room temperature until the solid had completely dissolved. The solution was then frozen and lyophilized to afford the desired product as a light pinkish solid.

The mesylate (5.8 g, 14.3 mmol) was crystallized by dissolution in a mixture of ethanol and toluene (3/25 v/v, 56 mL) at 100° C., and the mixture cooled to room temperature. Needle-like crystals started to form after standing at room temperature for 16 h. The solution was filtered after standing for 2 days at room temperature. The product (7) was isolated as a white crystalline solid (1.2 g, 21% yield). $^1$H-NMR (400 MHz, CD$_3$OD): δ 7.16-7.23 (m, 3H), 4.80-4.84 (dd, J=12.0, 4.4 Hz, 1H), 4.57-4.61 (dd, J=12.4 Hz, 3.2 Hz, 1H), 4.47-4.49 (dd, J=4.4, 2.8 Hz, 1H), 2.98-3.01 (m, 2H), 2.69 (s, 3H); 1.18-1.20 (dd, J=7.2, 1.6 Hz, 12H). MS (ESI) m/z 310.3 (M+H)$^+$. Melting point: 166.9-167.3° C.

Example 5

Preparation of Crystalline (R)-2-Amino-3-(2,6-Diisopropylphenoxy-carbonyloxy)-Propanoic Acid Hydrochloride (9)

Crystalline (R)-2-amino-3-(2,6-diisopropylphenoxy-carbonyloxy)-propanoic acid hydrochloride, (9), was prepared essentially as disclosed in Examples 1-4 by replacing (S)-Boc-Ser-Obn with (R)-Boc-Ser-Obn.

Example 6

X-Ray Power Diffraction (XRPD) Analysis of Crystalline (S)-2-Amino-3-(2,6-Diisopropylphenoxy-carbonyloxy)-Propanoic Acid Hydrochloride (6) and Crystalline (S)-2-Amino-3-(2,6-Diisopropylphenoxy-carbonyloxy)-Propanoic Acid Mesylate (7)

Figure 2:
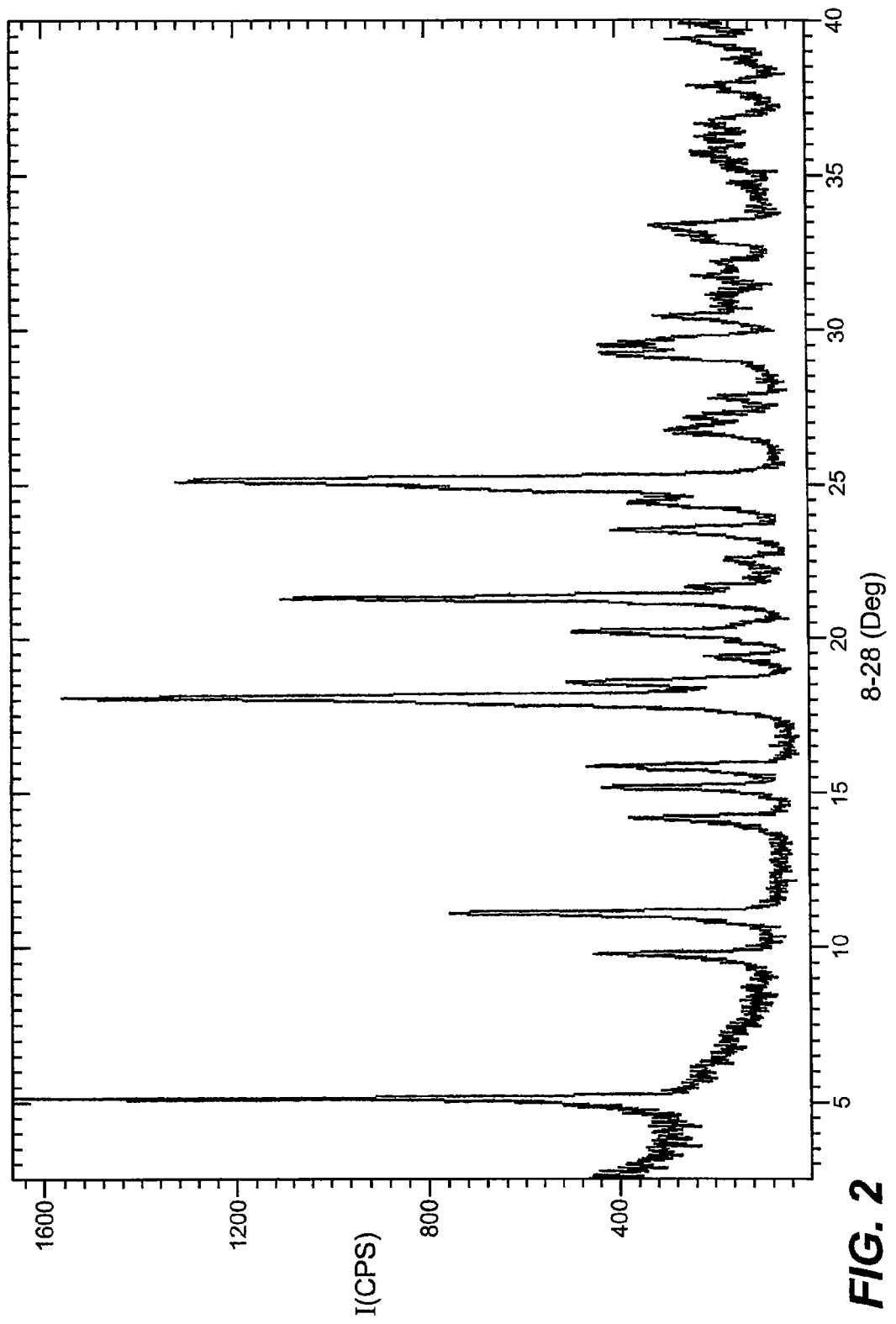
FIG. 2 illustrates an X-ray powder diffraction pattern of crystalline (S)-2-amino-3-(2,6-diisopropylphenoxy-carbonyloxy)-propanoic acid mesylate.

The XRPD analyses were performed using a Shimadzu XRD-6000 X-ray power diffractometer using Cu Kα radiation. The instrument was equipped with a long fine focus X-ray tube. The tube voltage and amperage were set to 40 kV and 40 mA, respectively. The divergence and scattering slits were set at 1° and the receiving slit was set at 0.15 mm. Diffracted radiation was detected using a NaI scintillation detector. A θ-2θ continuous scan at 3°/min (0.4 sec/0.02° step) from 2.5 to 40° 2θ was used. Instrument alignment was checked by analyzing a silicon standard. Data were collected and analyzed using XRD-6000 v.4.1. A representative diffraction pattern for compound (6) and compound (7) is shown in FIGS. 1 and 2, respectively. The presence of clearly resolved peaks is indicative of the crystalline nature of compounds (6) and (7).

Example 7

Uptake of Propofol Following Oral or Intravenous Administration of Prodrugs to Rats Step 1: Administration Protocol Propofol or propofol prodrug was administered as an intravenous bolus injection or by oral gavage to groups of four to six adult male Sprague-Dawley rats (weight approx 250 g). Animals were conscious at the time of the experiment. Propofol or propofol prodrug was orally administered as an aqueous solution at a dose equivalent to 25 mg of propofol per kg body weight. When administered intravenously, propofol was administered as a solution (Diprivan®, Astra-Zeneca) at a dose equivalent to 15 mg of propofol per kg body weight. Animals were fasted overnight before the study and for 4 hours post-dosing. Blood samples (0.3 mL) were obtained via a jugular vein cannula at intervals over 8 hours after oral dosing. Blood was quenched immediately using acetonitrile with 1% formic acid and then was frozen at −80° C. until analyzed.

Step 2: Sample Preparation for Absorbed Drug

1. In blank 1.5 mL tubes, 300 μL of 0.1% formic acid in acetonitrile was added.

2. Rat blood (300 μL) was collected at different times into EDTA tubes and vortexed to mix. A fixed volume of blood (100 μL) was immediately added into the Eppendorf tube and vortexed to mix.

3. Ten microliters of a propofol standard stock solution (0.04, 0.2, 1, 5, 25, 100 μg/mL) was added to 90 μL of blank rat blood quenched with 300 μL of 0.1% formic acid in acetonitrile. Then, 20 μL of p-chlorophenylalanine was added to each tube to make the to make up a final calibration standard (0.004, 0.02, 0.1, 0.5, 2.5, 10 μg/mL).

4. Samples were vortexed and centrifuged at 14,000 rpm for 10 min.

5. Supernatant was analyzed by LC/MS/MS.

Step 3: LC/MS/MS Analysis

An API 4000 LC/MS/MS spectrometer equipped with Agilent 1100 binary pumps and a CTC HTS-PAL autosampler were used in the analysis. A Phenomenex Synergihydro-RP 4.6×30 mm column was used during the analysis. The mobile phase for propofol analysis was (A) 2 mM ammonium acetate, and (B) 5 mM ammonium acetate in 95% acetonitrile. The mobile phase for the analysis of propofol prodrugs was (A) 0.1% formic acid, and (B) 0.1% formic acid in acetonitrile. The gradient condition was: 10% B for 0.5 min, then to 95% B in 2.5 min, then maintained at 95% B for 1.5 min. The mobile phase was returned to 10% B for 2 min. An APCI source was used on the API 4000. The analysis was done in negative ion mode for propofol and positive ion mode for propofol prodrugs. The MRM transition for each analyte was optimized using standard solutions. 5 μL of the sample was injected. Non-compartmental analysis was performed using WinNonlin (v.3.1 Professional Version, Pharsight Corporation, Mountain View, Calif.) on individual animal profiles. Summary statistics on major parameter estimates was performed for $C_{max}$ (peak observed concentration following dosing), $T_{max}$ (time to maximum concentration is the time at which the peak concentration was observed), $AUC_{(0-t)}$ (area under the serum concentration-time curve from time zero to last collection time, estimated using the log-linear trapezoidal method), $AUC_{(0-\infty)}$, (area under the serum concentration time curve from time zero to infinity, estimated using the log-linear trapezoidal method to the last collection time with extrapolation to infinity), and $t_{1/2,z}$ (terminal half-life).

The oral bioavailability (F) of propofol was determined by comparing the area under the propofol concentration vs time curve (AUC) following oral administration of propofol with the AUC of the propofol concentration vs time curve following intravenous administration of propofol on a dose normalized basis. Using this measurement technique, the oral bioavailability of propofol was found to be very low, as expected (F=0.23%).

Oral bioavailability (F) of propofol, resulting from oral administration of the propofol prodrug (6) of (7) in rats was determined by comparing the area under the propofol concentration vs time curve (AUC) following oral administration of the propofol prodrug (6) or (7) and with the AUC measured following intravenous administration of an equimolar dose of propofol itself. Prodrug (6) or (7) provided greater than 10% absolute oral bioavailability of propofol, i.e., compared to the bioavailability of propofol following intravenous administration of an equimolar dose of propofol itself. Thus, prodrug (6) or (7) provided at least about 40 times higher oral bioavailability of propofol compared to the oral bioavailability of propofol itself. The result illustrates that prodrugs of the present disclosure, when taken orally, provide therapeutically significant blood concentrations of propofol in rats.

Example 8

Uptake of Propofol Following Oral Administration of Prodrugs to Monkeys

Step 1: Administration Protocol

Test compounds were administered by oral gavage or as an intravenous bolus injection to groups of two to four adult male Cynomologous (*Macaca fascicularis*) monkeys (weight approx 5 kg) as solutions in water or PEG400 at a dose of 25 mg-equivalents of propofol per kg body weight. Animals were fasted overnight before the study and for 4 hours post-dosing. Blood samples (1.0 mL) were obtained via the femoral vein at intervals over 24 hours after oral dosing. Blood was quenched immediately using acetonitrile with 1% formic acid and then frozen at −80° C. until analyzed. Test compounds are administered in the monkeys with a minimum of 72-hour wash out period between dosing sessions.

Step 2: LC/MS/MS Analysis

Concentrations of propofol in quenched whole blood were determined using an API 4000 LC/MS/MS instrument equipped with an Agilent 1100 binary pump and an Agilent autosampler. The column was a Phenomenex Hydro-RP 4.6× 50 mm column operating at room temperature. The mobile phases were (A) 2 mM aqueous ammonium acetate, and (B) 95% acetonitrile with 5 mM ammonium acetate. The gradient condition was: 5% B for 1 min, increasing to 90% B in 2.5 min and maintained for 2 min. 20 μL of sample was injected. A Turbo-IonSpray source was used, and propofol was detected in negative ion mode in Q1 at m/z=177. Prodrugs were detected in positive ion mode and peaks were integrated using Analyst 1.2 quantitation software.

Oral bioavailability (F) of propofol resulting from oral administration of the propofol prodrug (8) of Example 1 in monkeys was determined by comparing the area under the propofol concentration vs time curve (AUC) following oral administration of a propofol prodrug with the AUC measured following intravenous administration of an equimolar dose of propofol itself. The above prodrugs provided greater than 10% absolute oral bioavailability of propofol, i.e., compared to the bioavailability of propofol following intravenous administration of an equimolar dose of propofol itself. Thus, prodrug (8) provided at least about 40 times higher oral bioavailability of propofol compared to the oral bioavailability of propofol itself. The results illustrate that prodrugs of the present disclosure, when taken orally, provide therapeutically significant blood concentrations of propofol in monkeys.

Example 9

Propofol Blood Concentrations Following Oral Administration of Propofol Prodrugs to Dogs Step 1: Administration Protocol Test compounds were administered by oral gavage or as an intravenous bolus injection to groups of two to four adult male Beagle dogs (weight approx 8 kg) as solutions in water or 4% Labrasol at a dose of 25 mg-equivalents to 300 mg-equivalents of propofol per kg body weight. Animals were fasted overnight before the study and for 4 hours post-dosing. Blood samples (1.0 mL) were obtained via the femoral vein at intervals over 24 hours after oral dosing. Blood was quenched immediately using acetonitrile with 1% formic acid and then frozen at −80° C. until analyzed. Test compounds were administered to the dogs with a minimum of 7-day wash out period between dosing sessions.

Step 2: LC/MS/MS Analysis

The bioavailability of propofol was determined by LC/MS/MS according to the procedure disclosed in Example 8, Step 3.

Oral bioavailability (F) of propofol, resulting from oral administration of the propofol prodrug (6) of Example 3 in dogs was determined by comparing the area under the propofol concentration vs time curve (AUC) following oral administration of a propofol prodrug with the AUC measured following intravenous administration of an equimolar dose of propofol itself. The above prodrugs provided greater than 10% absolute oral bioavailability of propofol, i.e., compared to the bioavailability of propofol following intravenous administration of an equimolar dose of propofol itself. Thus, prodrug (6) provided at least about 40 times higher oral bioavailability of propofol compared to the oral bioavailability of propofol itself. The results illustrate that prodrugs of the present disclosure, when taken orally, provide therapeutically significant blood concentrations of propofol in dogs.

Finally, it should be noted that there are alternative ways of implementing the present invention. Accordingly, the present embodiments are to be considered as illustrative and not restrictive, and the invention is not to be limited to the details given herein, but may be modified within the scope and equivalents of the claim(s) issuing herefrom.

What is claimed is:

1. A method of treating a disease or disorder selected from pain, headache, anxiety and emesis, in a patient comprising administering to a patient in need of such treatment a therapeutically effective amount of 2-amino-3-(2,6-diisopropylphenoxycarbonyloxy)-propanoic acid or a pharmaceutically acceptable salt thereof.

2. The method of claim 1, wherein the 2-amino-3-(2,6-diisopropylphenoxycarbonyloxy)-propanoic acid or a pharmaceutically acceptable salt thereof is (S)-2-amino-3-(2,6-diisopropylphenoxycarbonyloxy)-propanoic acid or a pharmaceutically acceptable salt thereof.

3. The method of claim 1, wherein the pharmaceutically acceptable salt is selected from a hydrochloride salt, a mesylate salt, and a trifluoroacetate salt.

4. The method of claim 2, wherein the pharmaceutically acceptable salt is selected from a hydrochloride salt, a mesylate salt, and a trifluoroacetate salt.

5. The method of claim 4, wherein the (S)-2-amino-3-(2,6-diisopropylphenoxycarbonyloxy)-propanoic acid or a pharmaceutically acceptable salt thereof is a crystalline form of a hydrochloride salt and having characteristic peaks (2θ) at 5.1°±0.2°, 11.0°±0.2°, 17.9°±0.2°, 21.3°±0.2°, and 25.1°±0.2° in an X-ray power diffraction pattern measured using Cu Kα radiation.

6. The method of claim 5, wherein the crystalline form of the hydrochloride salt has characteristic peaks (2θ) at 9.7°±0.2°, 14.1°±0.2°, 15.1°±0.2°, 15.8°±0.2°, 18.5°±0.2°, 19.4°±0.2°, 20.1°±0.2°, 21.7°±0.2°, 22.5°±0.2°, 23.5°±0.2°, 24.4°±0.2°, 26.8°±0.2°, 27.3°±0.2°, 27.8°±0.2°, 29.2°±0.2°, 29.6°±0.2°, 30.4°±0.2°, and 33.4°±0.2° in the X-ray powder diffraction pattern measured using Cu Kα radiation.

7. The method of claim 5, wherein the crystalline form of the hydrochloride salt has characteristic peaks (2θ) at 9.7°±0.2°, 14.1°±0.2°, 15.1°±0.2°, 15.8°±0.2°, 18.5°±0.2°, 20.1°±0.2°, 22.5°±0.2°, 23.5°±0.2°, 29.2°±0.2°, 29.6°±0.2°, and 33.4°±0.2° in the X-ray powder diffraction pattern measured using Cu Kα radiation.

8. The method of claim 5, wherein the crystalline form of the hydrochloride salt has an X-ray powder diffraction pattern as shown in FIG. 1.

9. The method of claim 5, wherein the crystalline form of the hydrochloride salt has a melting point from about 188° C. to about 189° C.

10. The method of claim 4, wherein the (S)-2-amino-3-(2,6-diisopropylphenoxycarbonyloxy)-propanoic acid or a pharmaceutically acceptable salt thereof is a crystalline form of a mesylate salt having characteristic peaks (2θ) at 4.2°±0.1°, 12.6°±0.1°, 16.8°±0.1°, 21.0°±0.1° and 25.3±0.1° in an X-ray power diffraction pattern measured using Cu Kα radiation.

11. The method of claim 10, wherein the crystalline form of the mesylate salt has characteristic peaks (2θ) at 11.7°±0.1°, 12.1°±0.1°, 18.4°±0.2°, 22.3°±0.1°, 22.8°±0.2°, 24.9°±0.2°, 26.7°±0.2°, and 29.6°±0.1° in the X-ray powder diffraction pattern measured using Cu Kα radiation.

12. The method of claim 10, wherein the crystalline form of the mesylate salt has a characteristic peak (2θ) at 29.6°±0.1° in the X-ray powder diffraction pattern measured using Cu Kα radiation.

13. The method of claim 10, wherein the crystalline form of the mesylate salt has an X-ray powder diffraction pattern as shown in FIG. 2.

14. The method of claim 10, wherein the crystalline form of the mesylate salt has a melting point from about 166° C. to about 167° C.

15. The method of claim 1, wherein the therapeutically effective amount of 2-amino-3-(2,6-diisopropylphenoxycarbonyloxy)-propanoic acid or a pharmaceutically acceptable salt thereof is provided as a pharmaceutical composition.

16. The method of claim 15, wherein the pharmaceutical composition is an oral formulation.

17. The method of claim 16, wherein the oral formulation is a sustained release oral formulation.

18. The method of claim 1, wherein the headache is migraine headache.

19. The method of claim 1, wherein the emesis is induced by a chemotherapeutic agent.

20. The method of claim 1, wherein the anxiety is preoperative anxiety.

21. The method of claim 1, wherein the emesis is chemotherapy-induced nausea and vomiting.

* * * * *